United States Patent
Jinbo et al.

[11] Patent Number: 6,129,987
[45] Date of Patent: Oct. 10, 2000

[54] METHOD OF MAKING A PIECE OF GLASS FOR MEASURING TRANSMITTANCE

[75] Inventors: Hiroki Jinbo, Kawasaki; Satoru Oshikawa; Hiroyuki Hiraiwa, both of Yokohama, all of Japan

[73] Assignee: Nikon Corporation, Japan

[21] Appl. No.: 09/067,035

[22] Filed: Apr. 23, 1998

Related U.S. Application Data

[62] Division of application No. 08/525,882, Sep. 8, 1995, Pat. No. 5,776,219.

[30] Foreign Application Priority Data

Sep. 8, 1994 [JP] Japan .................................. 6-215096

[51] Int. Cl.$^7$ ...................................................... B32B 17/00
[52] U.S. Cl. .......................... 428/426; 428/428; 428/432
[58] Field of Search ...................... 428/426, 428, 428/432

[56] References Cited

U.S. PATENT DOCUMENTS

| | | | |
|---|---|---|---|
| 3,123,452 | 3/1964 | Harris et al. | 51/307 |
| 3,310,495 | 3/1967 | Masuda et al. | 216/88 |
| 3,982,917 | 9/1976 | Upton | 65/31 |
| 4,106,859 | 8/1978 | Doriguzzi et al. | 349/113 |
| 4,198,788 | 4/1980 | Fleetwood et al. | 451/41 |
| 4,911,743 | 3/1990 | Bagby | 65/31 |

FOREIGN PATENT DOCUMENTS

| | | |
|---|---|---|
| 34 406 | 12/1964 | Germany . |
| 24 22 506 | 11/1975 | Germany . |
| 28 47 935 | 5/1980 | Germany . |
| 89 10 392 | 12/1989 | Germany . |
| 1-40267 | 2/1989 | Japan . |
| 1-40267 | 5/1989 | Japan . |
| 7-63680 | 3/1995 | Japan . |

OTHER PUBLICATIONS

Götz, J., Sprechsaal für keramik glas email silikate, Nr. 13, 101. Jg., 1968, S. 539–540, 542–544.

Kaller, A., On the polishing of glass, particularly the precision polishing of optical surfaces, In: Glastech. Ber. 64, 1991, Nr. 9, S. 241–252.

Japanese Optical Glass Industrial Standards, "Appendix: Explanations on Measuring Method of Optical Glass," Translated and Published by Japan Optical Glass Manugacturer's Association, Mar. 3, 1975.

Akimaya, "The Precise Spectral Transmission Measuring Method for the Optical Glases" (w/English Abstract), 1992.

*Primary Examiner*—Timothy M. Speer
*Attorney, Agent, or Firm*—Pennie & Edmonds LLP

[57] ABSTRACT

In the measurement of internal transmittance of optical pieces, a standard is set for the piece for measuring the transmittance and a method of making the piece is provided. In the piece for measuring the Transmittance of optical materials having two opposing polished surfaces, their surface roughness rms is set to 10 Å or less, thereby making it possible to accurately measure the internal transmittance in the short wavelength region of 300 nm or less where the intensity of the light source of spectrophotometer begins to decrease.

18 Claims, 28 Drawing Sheets

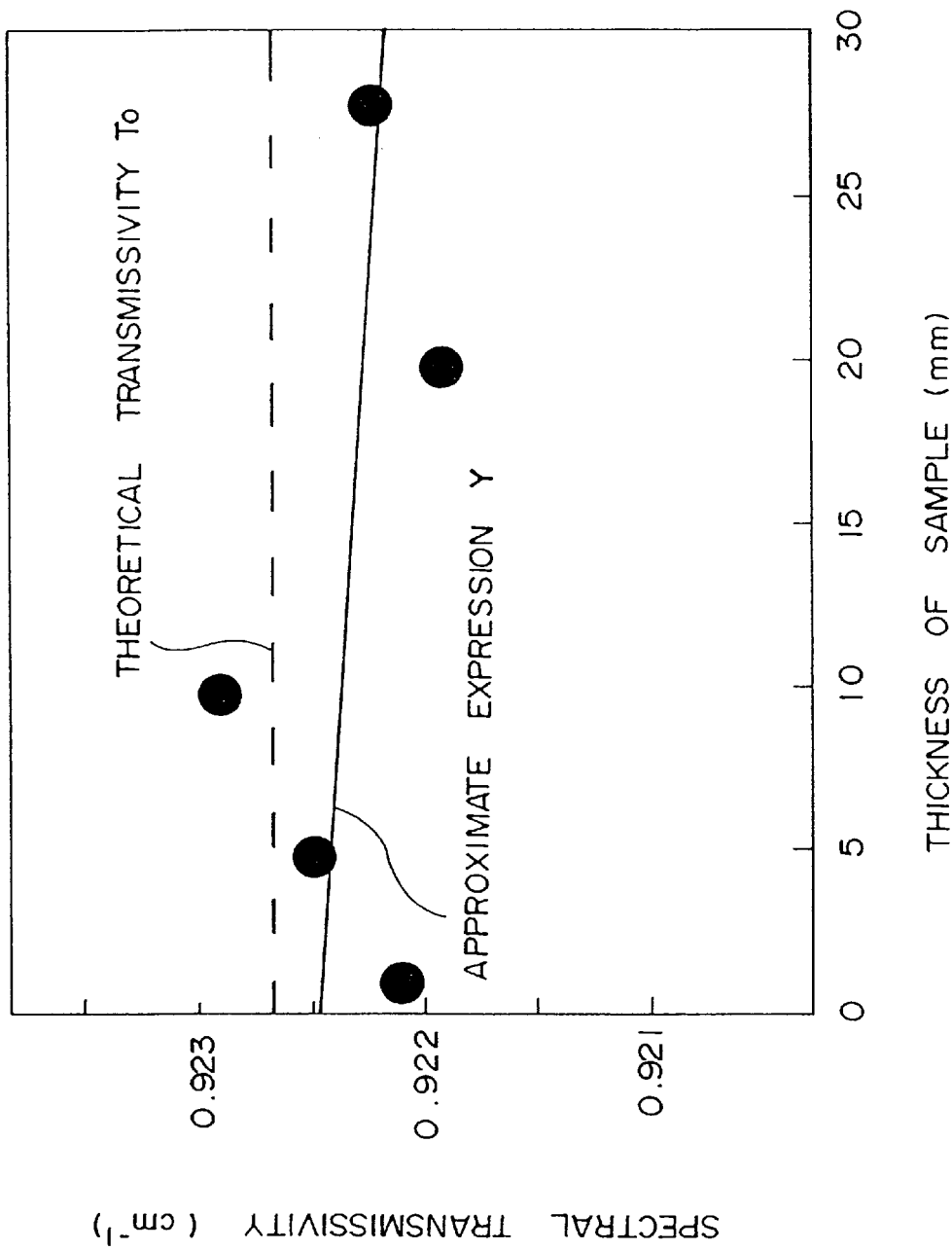

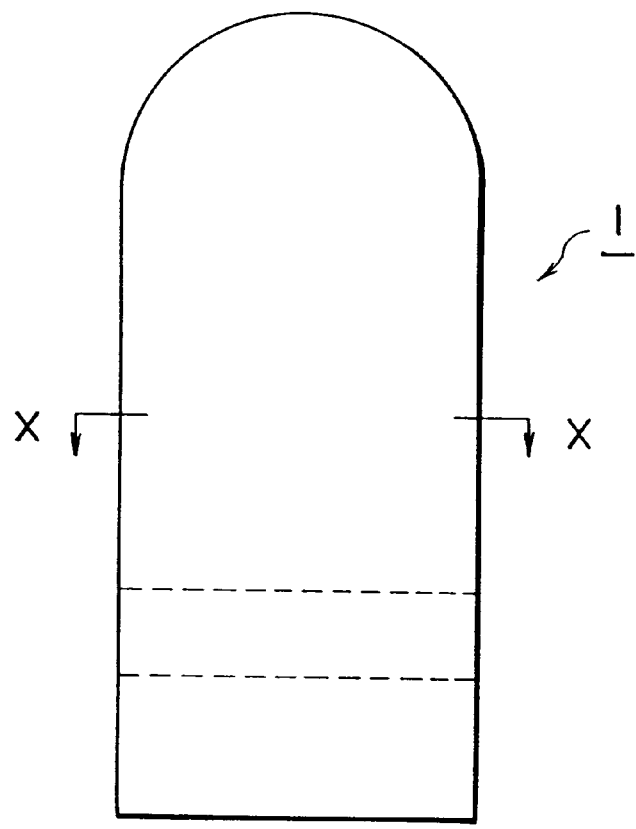
Fig. IIA
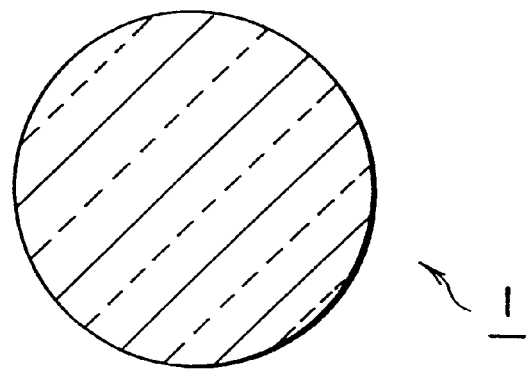
Fig. IIB

METHOD OF MAKING A PIECE OF GLASS FOR MEASURING TRANSMITTANCE

This is a divisionnal of application Ser. No. 08/525,882 filed Sep. 8, 1995, now U.S. Pat. No. 5,776,219.

BACKGROUND OF THE INVENTION

Field of the Invention

The present invention relates to a piece (sample) used for accurately measuring transmittance, e.g. internal transmittance (spectral transmittance excluding reflection loss), of optical materials such as multicomponent glass, synthetic silica glass, and crystal materials as well as a method of making such a piece in particular, it relates to a piece for measuring the transmittance of multicomponent glass used in visible-ultraviolet optical systems, such as g-beam (436 nm) and i-beam (365 nm) lithography techniques and synthetic silica glass and crystal materials used in ultraviolet optical systems in the range of 300 nm or less such as KrF (248 nm) and ArF (193 nm) excimer laser lithography techniques.

Related Background Art

An exposure apparatus called "stepper" has conventionally been used in a photolithography technique in which a fine pattern of integrated circuits is exposed to light and transferred to a wafer made of silicon or the like. The wavelength of the light source of the stepper has been becoming shorter as the integration of LSI increases.

SUMMARY OF THE INVENTION

It is necessary for the optical glass used in the illuminating system or projection lens of such a stepper to have an internal transmittance of 0.998 $cm^{-1}$ or 0.999 $cm^{-1}$ or more (i.e. internal absorption coefficient of 0.002 $cm^{-1}$ or 0.001 $cm^{-1}$ or less). As the LSI is further integrated, the light source of the stepper is shifting toward KrF and ArF excimer lasers. In the illuminating system or projection lens of such an excimer laser stepper, generic optical glass cannot be used any more. The material used for this purpose is restricted to such a material as silica glass or fluorite. It is also necessary for silica glass or fluorite used in the illuminating system or projection lens to have an internal transmittance of 0.998 $cm^{-1}$ or 0.999 $cm^{-1}$ or more. Accordingly, development has been in progress to increase the transmittance of the above-mentioned optical materials in the ultraviolet region. As the wavelength becomes shorter, on the other hand, it has become technically very difficult to accurately measure the internal transmittance of the optical materials. Therefore, in the first place, in order to attain an optical material with a high transmittance, it is necessary to provide a technique by which the internal transmittance of optical glass, synthetic silica glass, crystal material, or the like with only a weak absorption (with an internal absorption coefficient of about 0.001 $cm^{-1}$) can accurately be measured and evaluated.

As a method for measuring the internal transmittance, Japanese Optical Glass Industrial Standard JOGIS-17-82 defines a method for measuring the internal transmittance of optical glass. This method applies similarly to other optical materials such as silica glass or crystal materials when the internal transmittance of such materials are to be measured. According to this standard, a pair of pieces for determining the transmittance respectively having thicknesses of 3 mm and 10 mm are prepared, opposite surfaces of both pieces are polished in parallel to each other, the internal transmittance is indicated as a value with reference to the 10 nm-thick glass, and the value is rounded off to three decimal places. Therefore, the accuracy in measurement corresponds to an internal absorption coefficient of only 0.01 $cm^{-1}$ and cannot be applied to short wavelength regions such as those of i-beam and excimer laser where problems of errors in measuring the internal transmittance become critical.

In view of the foregoing, in order to measure an internal absorption coefficient of 0.001 $cm^{-1}$ as a significant difference in the method for measuring the transmittance of optical materials, the inventors of the present invention have studied the following options:

1) Using a spectrophotometer with a high basic performance to determine the spectral transmittance (i.e. transmittance including reflection loss).

2) Compensating for a shift in transmittance due to a shift in an optical path caused by a piece inserted within the measurement optical path.

3) Making a piece (sample) with a high accuracy, namely, with few measurement errors.

In 1), it is preferable that the stray light in the measurement optical path or the measurement light noise of the measurement light detecting portion or the like should be in the range of ±0.0002 $cm^{-1}$ or less. This level can be achieved when the kinds of commercial spectrophotometer are selected and their measuring condition is optimized.

The feature of 2) can be attained when the optical path of the spectrophotometer is adjusted and a calibration curve for the thickness of the optical material is determined and corrected with reference to Japanese Patent Application No. 5-211217 titled "METHOD OF MEASURING INTERNAL TRANSMITTANCE AND METHOD OF ADJUSTING SPECTROPHOTOMETER."

As For 3), there has conventionally been no standard for a sample used for measuring transmittance. Namely, items and levels have not been quantified for specifying the sample. Accordingly, no method has been indicated for making the piece for measuring transmittance which embodies the standard thereof.

The present invention relates to 3) and aims at setting a standard for a sample for measuring Transmittance in the measurement of the internal transmittance of optical materials and providing a method of making such a sample. The object of the present invention is to thereby measure an internal absorption coefficient of 0.001 $cm^{-1}$ as a significant difference and, in particular, to accurately measure the transmittance in the measurement of the internal transmittance in a short wavelength region of 300 nm or less where the intensity of the light source of spectrophotometer begins to decrease.

For long years, in the method of measuring the transmittance of the optical materials, the inventors have diligently studied errors in the measurement caused by the standard of the sample for measuring the transmittance and by the method of making the same.

In the first place, the inventors have studied the element of errors in measurement caused by the sample to find out that the parallelism, surface accuracy, and surface roughness of the polished surface of the sample can be problematic.

Therefore, as a standard for a sample for measuring the transmittance of optical materials, there is provided a standard that the sample should have a parallelism of 30 seconds or less, a surface accuracy of the same order as the parallelism or less, and a surface roughness rms of 10 Å or less.

In general, a part of the optical material to be evaluated is cut out into a shape which can fit into a sample chamber of the spectrophotometer and its two surfaces opposing to each other in the thickness direction are optically polished with a commercial abrasive agent to provide the aimed sample.

The parallelism used herein refers to an inclination (angle) with respect to a reference surface which is one of the two opposing optically-polished surfaces. The surface accuracy refers to an amount of deviation of the polished surface from a plane prototype. The surface roughness refers to the height of irregularities in each optically-polished surface.

Further, it has been found that the spectral transmittance of optical materials decreases due to the structural defects resulting from residual impurities such as cutting and abrasive agents used for making the sample and residual stress generated upon processing of the sample. Accordingly, the present invention provides a method of making a sample for measuring transmittance characterized in that the sample is prepolished to have a surface roughness rms of about 10 Å and then polished with an $SiO_2$ abrasive agent to have a surface roughness rms of 10 Å or less or treated with an acid or alkali.

The piece according to the present invention, a transmittance of not less than 0.910 $cm^{-1}$ and not more than 0.921 $cm^{-1}$ with respect to a light beam having a wavelength of 248 nm. The piece according the present invention, a transmittance of not less than 0.895 $cm^{-1}$ and not more than 0.908 $cm^{-1}$ with respect to a light beam having a wavelength of 193 nm. The piece according to the present invention, wherein fluorine exists on said first flat surface and said piece has a transmittance of not less than 0.9210 $cm^{-1}$ and not more than 0.9211 $cm^{-1}$ with respect to a light beam having a wavelength of 248 nm. The piece according to the present invention, wherein fluorine exists on said first flat surface and said piece has a transmittance of not less than 0.905 $cm^{-1}$ and not more than 0.908 $cm^{-1}$ with respect to a light beam having a wavelength of 193 nm.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 10 is a graph plotting the results of measurement of the 193 nm spectral transmittance of fluorite $CaF_2$ in accordance with EXPERIMENT 3 of the present invention.

FIG. 11A shows a glass ingot.

FIG. 11B is a cross-sectional view of the glass ingot taken along the line X—X of FIG. 11A.

DESCRIPTION OF THE PREFERRED EMBODIMENTS

In the following, embodiments of the present invention will be explained.

In order to make a piece of glass, an ingot 1 shown in FIG. 11A is used. FIG. 11B shows a cross-section of the ingot 1 taken along the line X—X. This cross section is circular.

A silica glass ingot with a high purity, which is an optical material, was synthesized by a process comprising the steps of preparing, as a raw material, silicon tetrachloride with a high purity; using a burner made of silica glass to mix and burn oxygen gas and hydrogen gas; diluting the raw-material gas with a carrier gas (which is usually oxygen gas) from the center portion so that the former gas gushes out; depositing the gushed material on a target; and melting the deposited material. In this way, a silica glass ingot having a diameter of 180 mm and a length of 550 mm was obtained.

Figure 12:
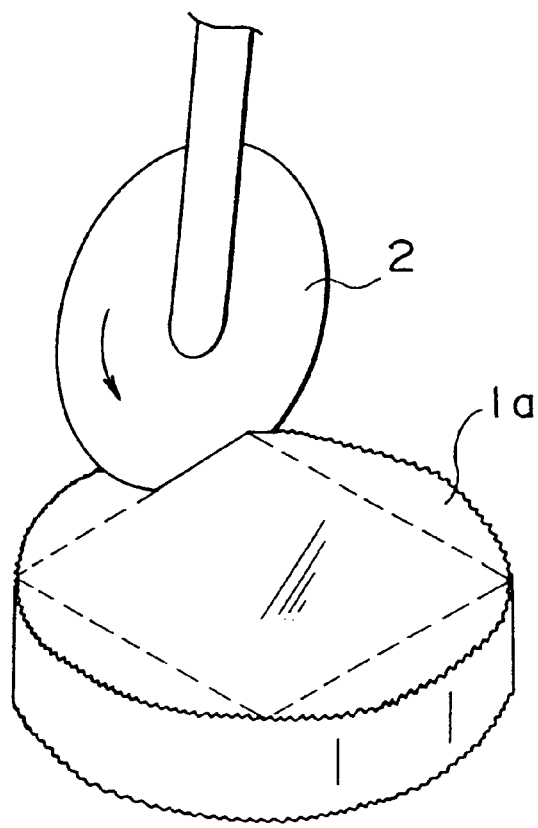
FIG. 12 shows a way of cutting a glass piece which has been cut out from the glass ingot of FIG. 11A.
Figure 13:
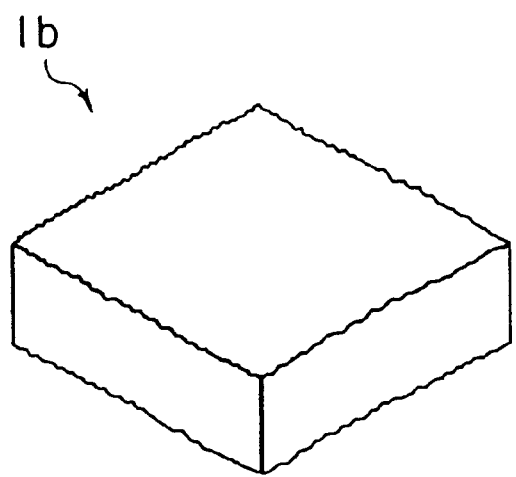
FIG. 13 shows a glass piece which has been processed into a square form.

In the first place, a glass piece 1a is cut out from the ingot 1 along a plane perpendicular to the center axis of the ingot 1. Then, as shown in FIG. 12, a diamond saw 2 is used to cut the glass piece 1a in its thickness direction to form a glass piece 1b such as the one shown in FIG. 13. The surfaces of the glass piece 1b are rough.

Figure 14:
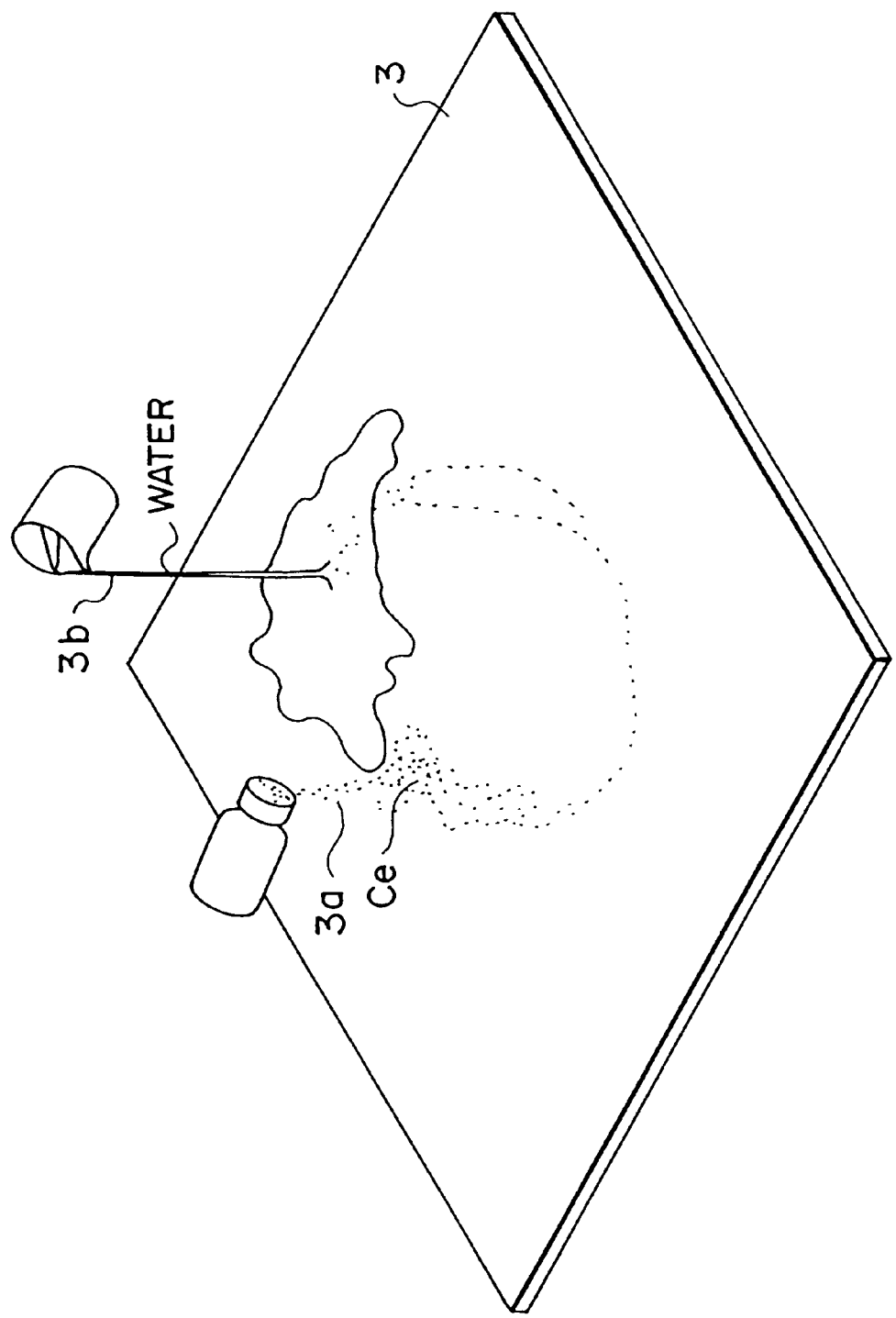
FIGS. 14–17 are drawings for explaining a polishing method.
Figure 15:
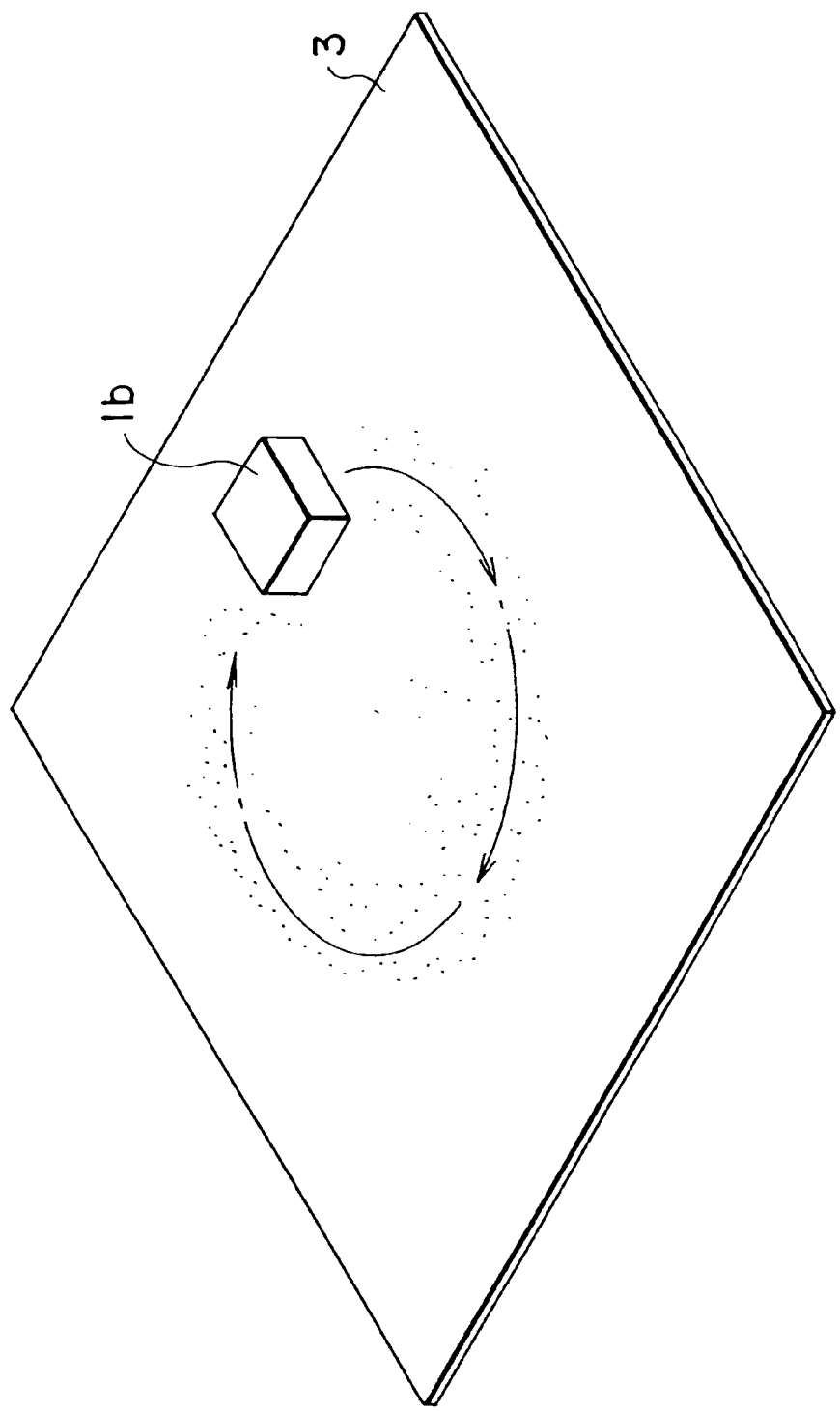
Figure 18:
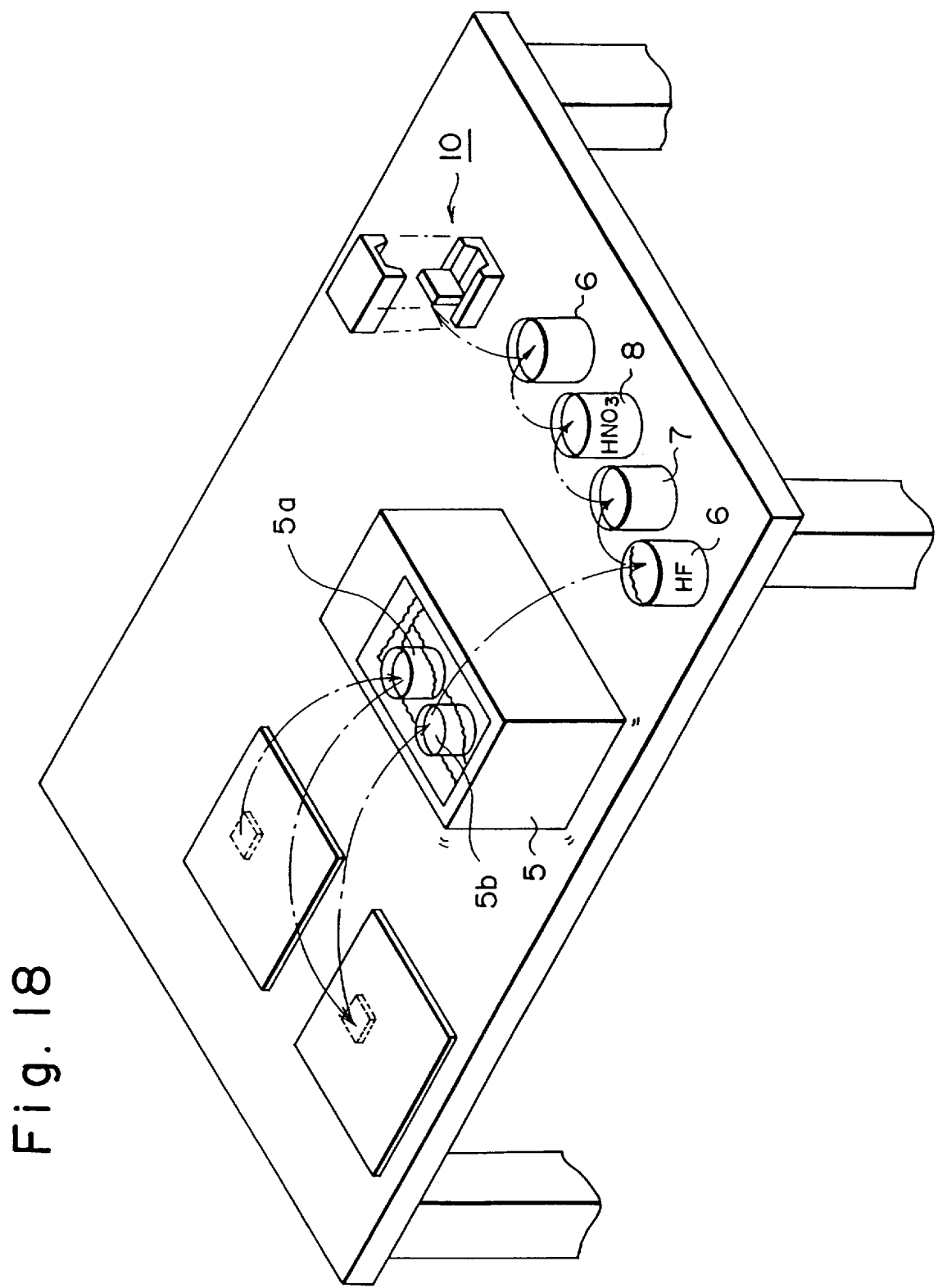
FIG. 18 shows a unit for manufacturing a sample.

Thereafter, a manufacturing unit shown in FIG. 18 is used to process the glass piece. At first, as shown in FIG. 14, an abrasive agent 3a made of cerium (Ce) is dispersed over glass sheet 3. Then, the glass sheet 3 is sprinkled with water 3b such that the abrasive agent 3a and water 3b are mixed together. As shown in FIGS. 1–5, the glass piece 1b is moved on the glass sheet 3 in a circle so as to polish its upper and lower surfaces.

A surface roughness meter is used to examine the surface roughness of the glass piece 1b. When the surface roughness falls down to 100 Å or less, the glass piece 1b is placed within a container 5a in an ultrasonic cleaner 5 to drop off Ce from the surface thereof. The container 5a has been filled with deionized water. The glass piece 1b is washed within this container 5a for 5 minutes.

Figure 16:
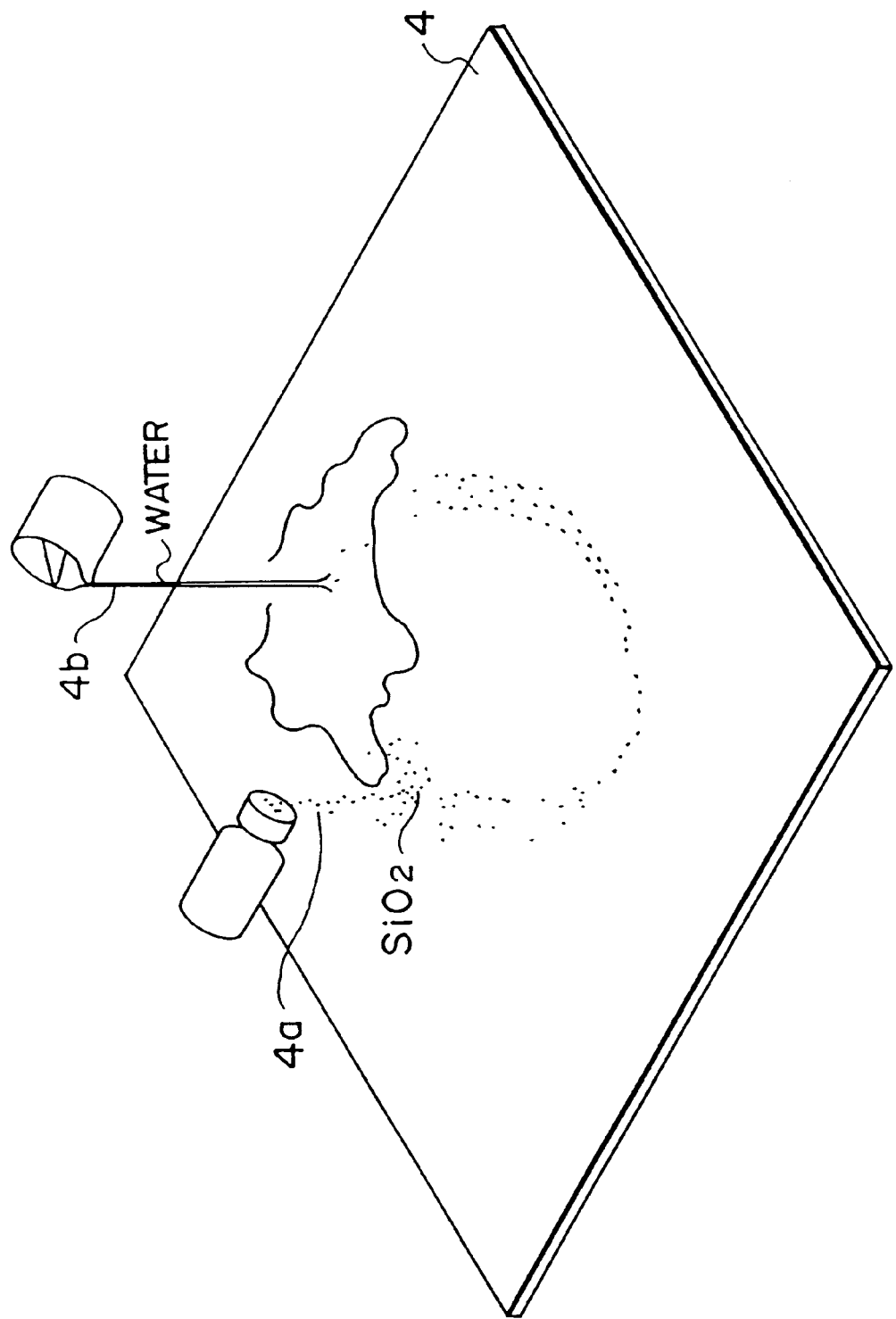
Figure 17:
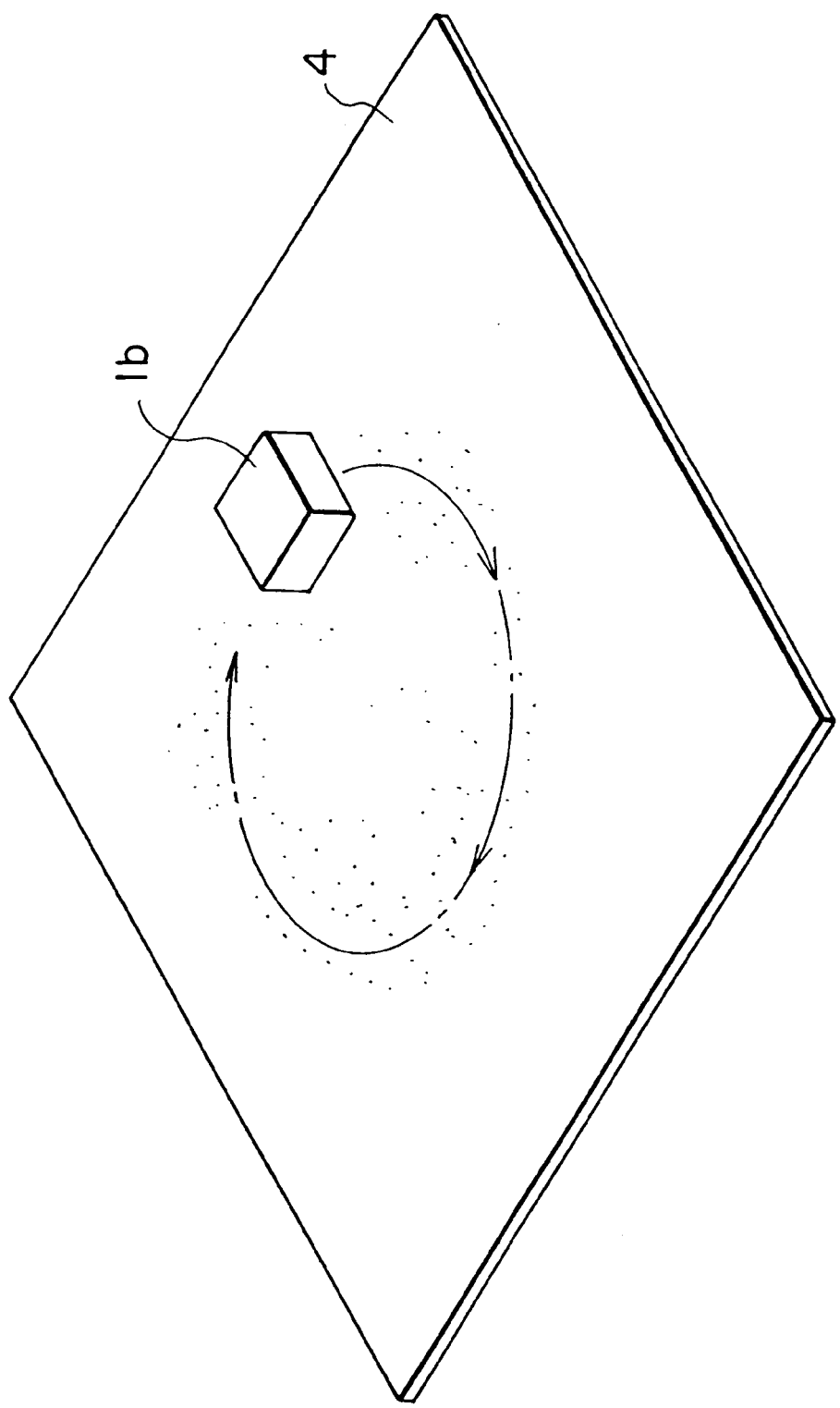

Thereafter, an abrasive agent 4a made of $SiO_2$ is used to further polish the glass piece 1b. As shown in FIG. 16, the abrasive agent 4a is dispersed over a glass sheet 4. Then, the glass sheet 4 is sprinkled with water 4b such that the abrasive agent 4a and water 4b are mixed together. As shown in FIG. 17, the glass piece 1b is moved on the glass sheet 4 in a circle so as to polish its upper and lower surfaces. A surface roughness meter is used to examine the surface roughness of the glass piece 1b. When the surface roughness of the glass piece 1b falls down to 10 Å or less, the polishing step is over. The surfaces of the glass sheets 3, 4 are flat.

As noted above, the surface roughness meter is used to examine the surface roughness of the glass piece 1b. When the surface roughness falls down to 10 Å or less, the glass piece 1b is placed within a container 5b in the ultrasonic cleaner 5 to drop off $SiO_2$ from the surface thereof. The container 5b has been filled with deionized water. The glass piece 1b is washed within this container 5b for 5 minutes.

Thereafter, the glass piece 1b is taken out from the container 5b and placed within a container 6 which has been filled with an aqueous fluoric acid (HF) solution. The glass piece 1b is immersed in an aqueous fluoric acid solution having a concentration of 5–20% by weight at 15–30° C. for 30 seconds to 3 minutes. Then, the glass piece is taken out from the container 6 and placed within a container 7 which has been filled with deionized water.

Thereafter, the glass 1b is taken out from the container 7 and placed within a container 8 which has been filled with nitric acid. The glass piece 1b is immersed in an aqueous nitric acid solution having a normality of 0.01–0.05 at 15–30° C. for 1–3 minutes.

Then, the glass piece 1b is taken out from the container 8 and placed within a container 9 which has been filled with aqueous ammonia. The glass piece is immersed in an aqueous ammonia solution having a normality of 0.001–0.05 at 15–30° C. for 1–3 minutes.

Finally, the glass piece 1b is taken our from the container 9 and dried while being supported by its four corners alone.

Figure 19:
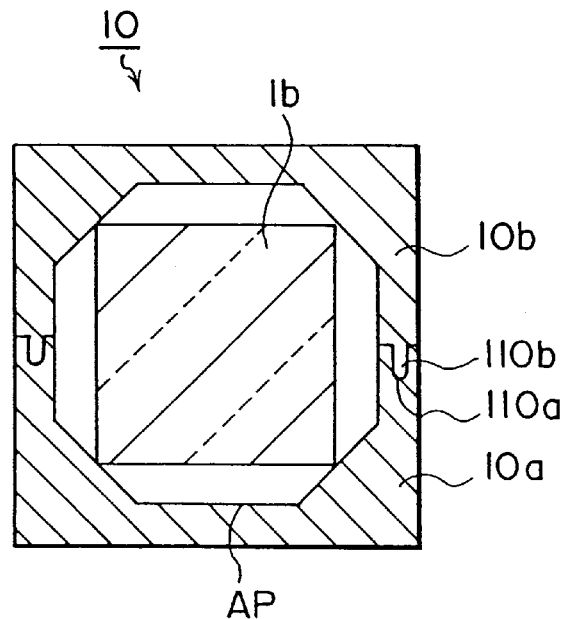
FIG. 19 shows a cross-sectional view of a sample holder.

A special holder 10 is used for supporting the glass piece 1b. FIG. 19 shows a cross-sectional view of the holder 10. This holder 10 comprises a lower member 10a and an upper member 10b. When these members are combined together, the cross section of the holder 10 has an opening AP which is in an equilateral octagon shape. The opening AP is defined by eight sides. The four corners of the glass piece 1b abut to four of these eight sides. The opening AP is constructed when a gutter formed on the lower member 10a and a gutter formed on the upper member 10b are combined together. Accordingly, when the glass piece 1b is placed within the gutter of the lower member 10a and then held by the inner surface of the gutter of the upper member 10b, the glass piece 1b is supported within the opening AP. On the upper surface of the lower member 10a, a hole 110a is formed to receive a protrusion 110b of the upper member 10b so that the glass piece 1b is fixed within the holder 10.

Figure 20A:
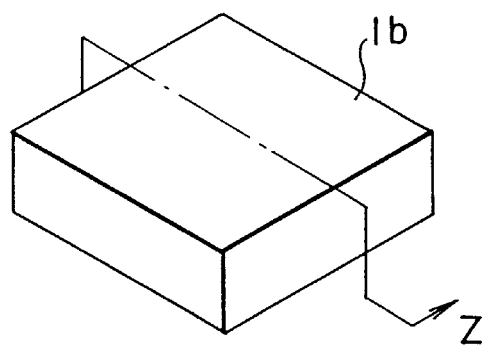
FIG. 20A shows a sample which has been polished and etched.
Figure 20B:
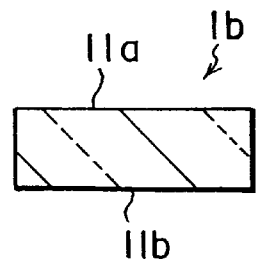
FIG. 20B is a cross-sectional view of the sample taken along the line Z of FIG. 20A.

FIG. 20A shows the dried glass sheet (piece) 1b. FIG. 20B is a cross-sectional view of the glass piece 1b taken along the line Z of FIG. 20A. The sample 1b has a pair of flat surfaces 11a, 11b opposing to each other. The angle of these surfaces 11a, 11b with respect to each other is 30 seconds or less. The roughness of each of the surfaces 11a, 11b is 10 Å or less.

The shift in measurement light which influences the parallelism and transmittance of the sample is expressed by the following equation:

$$\Delta X = \theta 1$$

wherein $\Delta X$ is the amount of displacement of the measurement light on a detector, $\theta$ is the parallelism of the sample, and 1 is the distance between the sample and the detector.

This equation indicates it necessary to define the parallelism of the sample in order to relatively compare transmittance values. Also, as the direction of the sample with respect to the measurement light determines the direction of displacement of the measurement light on the detector, it is necessary for the direction of inclination of the sample lo be aligned, preferably, at the time of measurement. However, the results of our experiment have shown that errors in measurement can be neglected when the parallelism is 30 seconds or less.

A fringe-scan type interferometer was used to measure the surface accuracy.

Figure 33:
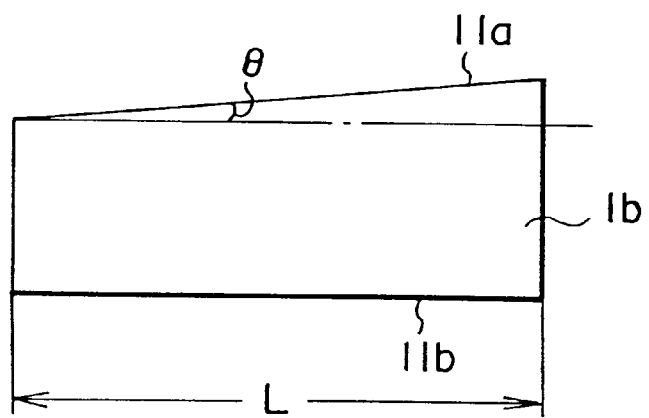
FIGS. 33–34 are cross sectional views of a piece.
Figure 34:
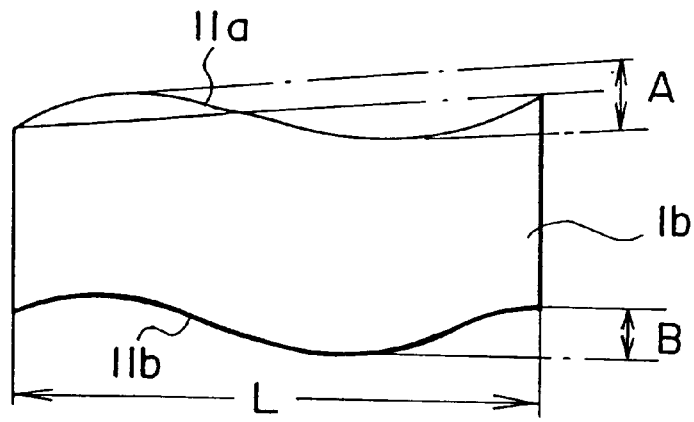

The surface accuracy which provides a vertical difference in the same order as the above-defined parallelism (30") of the sample can be obtained from the following equations:

surface accuracy $= d\lambda$ $d = \tan(30") \times L/\lambda/2$ wherein $\lambda$ is the wavelength of the measurement light which is usually 546 nm, 2 is the number of the surfaces, L is the maximum length (cm) of the polished surface of the sample such as its diameter or diagonal line length. Accordingly, the surface accuracy of $1.33L\lambda$ or less is necessary. It has been found that there are no problems concerning the accuracy in measurement when the actually measured surface accuracy is set at a value not more than the surface accuracy obtained from the above equations. From the above equations, d is determined as d=1.33L. The parallelism and the surface accuracy is explained in more detail using FIGS. 33 and 34, respectively. The parallelism is defined as an angle $\theta$ between the lower surface 11b and the upper surface 11a. The surface accuracy is defined as a total length (A+B) as shown in FIG. 34. The length A is a maximum distance between parallel two virtual planes each of which abuts a predetermined point on the diagonal line of upper surface 11a. The length B is a maximum distance between parallel two virtual planes each of which abuts a predetermined point on the diagonal line of lower surface 11b. The length (A+B) is less than 8 times λ4368 nm.

As to the surface roughness, in particular, the inventors have conducted experiments for examining the sample standard by taking account of the fact that the spectral transmittance of optical materials is measured lower than the theoretical transmittance calculated from their refractive index. An example of these experiments will be explained below.

In the first place, the theoretical transmittance will be explained. The spectral transmittance T in consideration of multiple reflection is defined by the following equations (1) and (2):

$$T = \frac{(1-R)^2 \times e^{-a \cdot t}}{1 - R^2 \times e^{-2-a-t}} \quad (1)$$

wherein a is the absorption coefficient, t is the thickness of the sample, and R is the reflectivity when the measurement light is vertically incident on the surface of the optical material.

$$R = \frac{(n_g - n_0)^2}{(n_g + n_0)^2} \quad (2)$$

wherein $n_g$ is the refractive index of the sample and $n_0$ is the refractive index of the air.

The theoretical transmittance $T_0$ is calculated as the spectral transmittance in equation (1) when the decrease in the amount of light results from reflection loss alone, i.e. the internal absorption coefficient a is zero, or when the thickness of the sample is infinitesimal.

In general, one of the reasons why the spectral transmittance is calculated lower than the theoretical transmittance, i.e. there is surface loss in the amount of measured light, has been attributed to the scattering loss resulting from the surface roughness of the sample.

Figure 1:
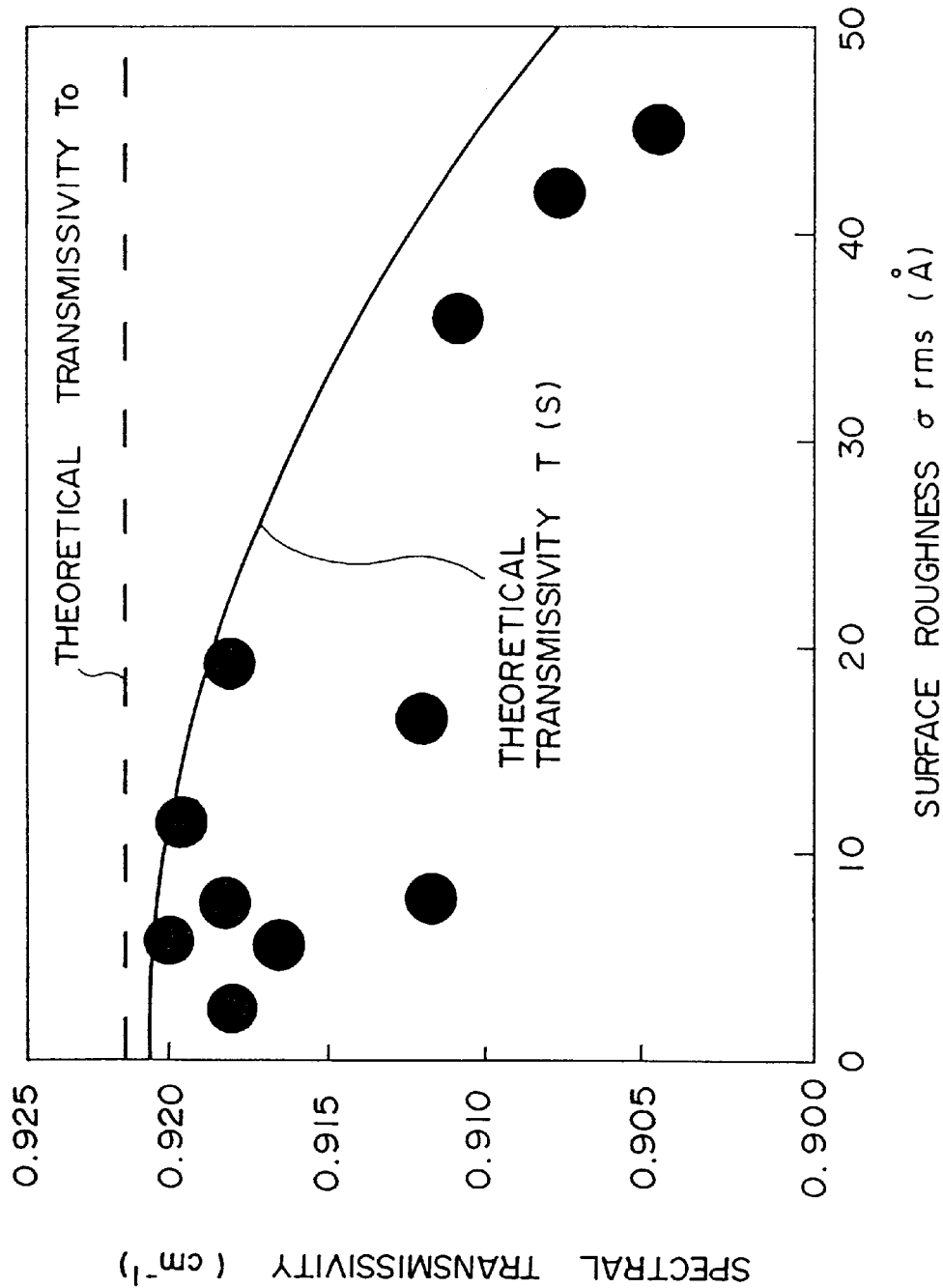
FIG. 1 is a graph plotting the relationship between the surface roughness of a sample and its various transmittance values (248 nm).
Figure 2:
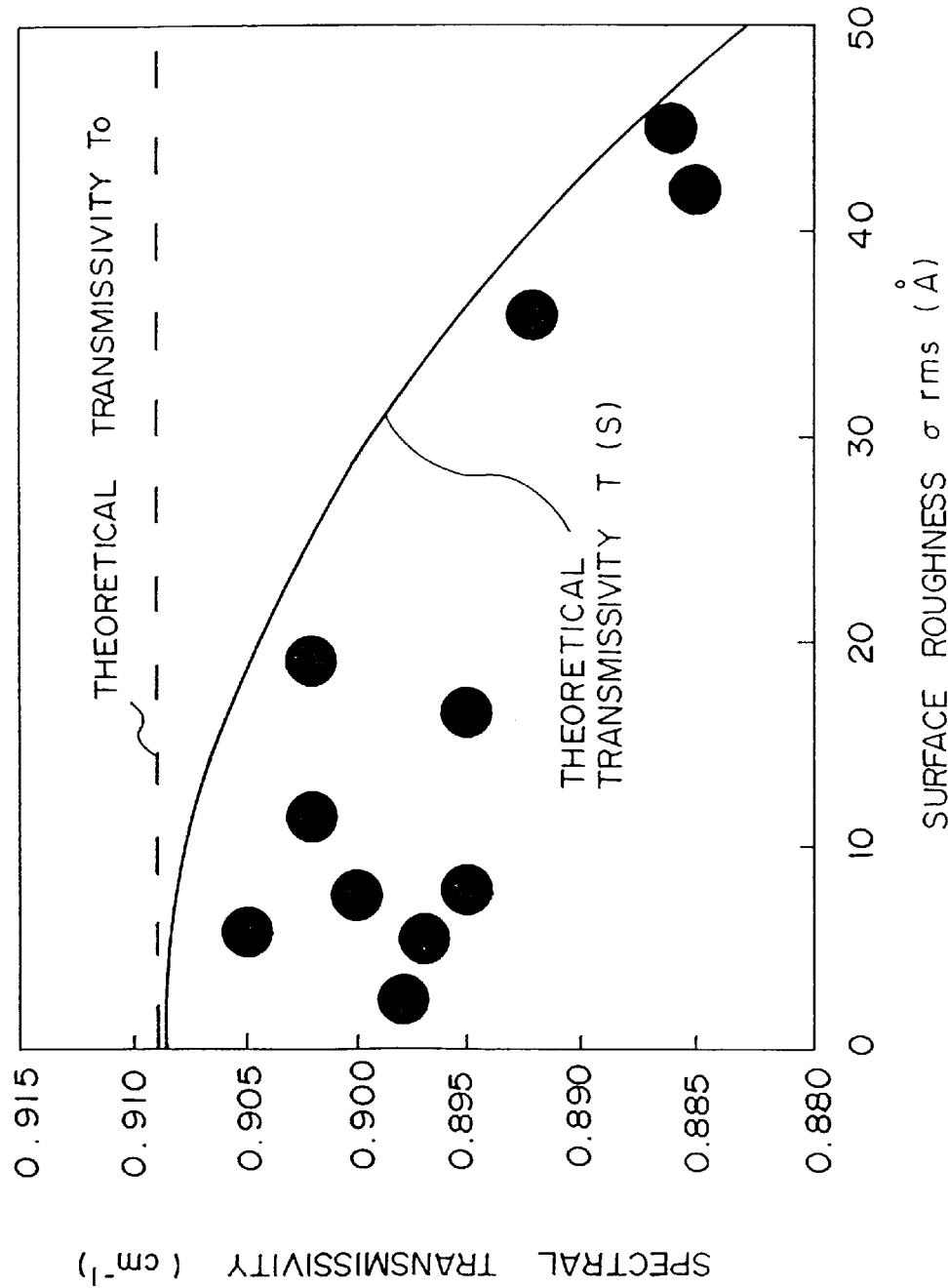
FIG. 2 is a graph plotting the relationship between the surface roughness of a sample and its various transmittance values (193 nm).

FIGS. 1 and 2 show relationships between the surface roughness of the sample and the theoretical transmittance excluding the scattering loss at measuring wavelengths of 248 nm and 193 nm, respectively.

The theoretical transmittance T(S) excluding the scattering loss is calculated according to the following equation:

$$T(S) = \{t-(S1^r+S1^t)\}\{t-(S2^r+S2^t)\}[1+\{R-(S2^r+S2^t)\}^2]$$

wherein R is the reflectivity, t is the spectral transmittance i-R after passing through the first surface, $S1^r$ is the scattering loss of the reflected light at the first surface, $S1^t$ is the scattering loss of the transmitted light at the first surface, $S2^r$ is the scattering loss of the reflected light at the second surface, and $S2^t$ is the scattering loss of the transmitted light at the second surface.

The scattering loss values $S1^r$, $S1^t$, $S2^r$, and $S2^t$ are calculated by the following equations:

$$S1^r = r(4\pi\sigma/\lambda)^2$$

$$S1^t = t\{2\pi(n-1)\sigma/\lambda\}^2$$

$$S2^r = r(4\pi\sigma/\lambda)^2$$

$$S2^t = t\{2\pi(n-1)\sigma/\lambda\}^2$$

wherein a is the surface roughness rms of the sample (root mean square) expressed by Å, n is the refractive index of the sample, and λ is the wavelength of the measuring light.

Synthetic silica glass samples which had been made in the same manner except for their surface roughness values to have a parallelism of 30 seconds, a surface accuracy of 3λ, and a thickness t of 10±0.05mm were used as samples for measuring the spectral-transmittance values with respect to various surface roughness levels shown in the drawings.

The surface roughness can be measured by an optical interference type surface roughness meter and determined by the following equation:

$$rms = \sqrt{\frac{\sum d(x,y)^2}{n}}$$

wherein d(x,y) is the vertical difference at the position of (x,y) and n is the number of the whole data within the range of measurement.

As can be seen from FIGS. 1 and 2, the theoretical transmittance value excluding the scattering loss shifts from the theoretical transmittance at the measuring wavelength, i.e. 0.921194 cm$^{-1}$ at 248 nm and 0.908734 cm$^{-1}$ at 193 nm, as the surface roughness of the sample increases.

These results indicate that, in order to secure the measuring accuracy, it is theoretically necessary for a standard for the sample for measuring the transmittance to have a surface roughness of 10 Å or less.

In view of the foregoing, in the method of measuring the transmittance of the optical materials, the present invention provides a standard for the sample for measuring the transmittance that the sample has a parallelism of 30 seconds or less, a surface accuracy in the same order as the parallelism or less, and a surface roughness rms of 10Å or less, thereby making it possible to stably measure the internal absorption coefficient of 0.001 cm$^{-1}$ as a significant difference.

However, it is understood that the spectral transmittance is not only be influenced by the surface roughness but can be measured lower than the theoretical transmittance excluding the scattering loss by 0.001 cm$^{-1}$ or more. This phenomenon is remarkable, in particular, at the short wavelength of 193 nm.

Therefore, the inventors have further diligently studied the method of measuring the transmittance of optical materials and investigated the method of making the sample for measuring the transmittance. As noted above, since the surface loss which causes the-.spectral transmittance to decrease cannot be explained by the scattering loss alone, various measurements on the surface of the sample have been conducted.

The residual impurities on the surface of the sample could not quantitatively be analyzed by normal surface analysis methods such as ESCK (electron spectroscopy for chemical analysis or X-ray photoelectron spectroscopy) and X-ray fluorescence analyzer since there are problems concerning their sensitivity. Accordingly, a total reflection X-ray fluorescence analyzer was used for analysis. The results are as follows:

a) A plenty of Ce impurities were detected on the surface of the sample whose spectral transmittance had been detected particularly low.

b) The spectral transmittance at 193 nm was measured lower in some of the samples in which Ce impurities could not be detected by the total X-ray fluorescence analysis method.

Figure 3:
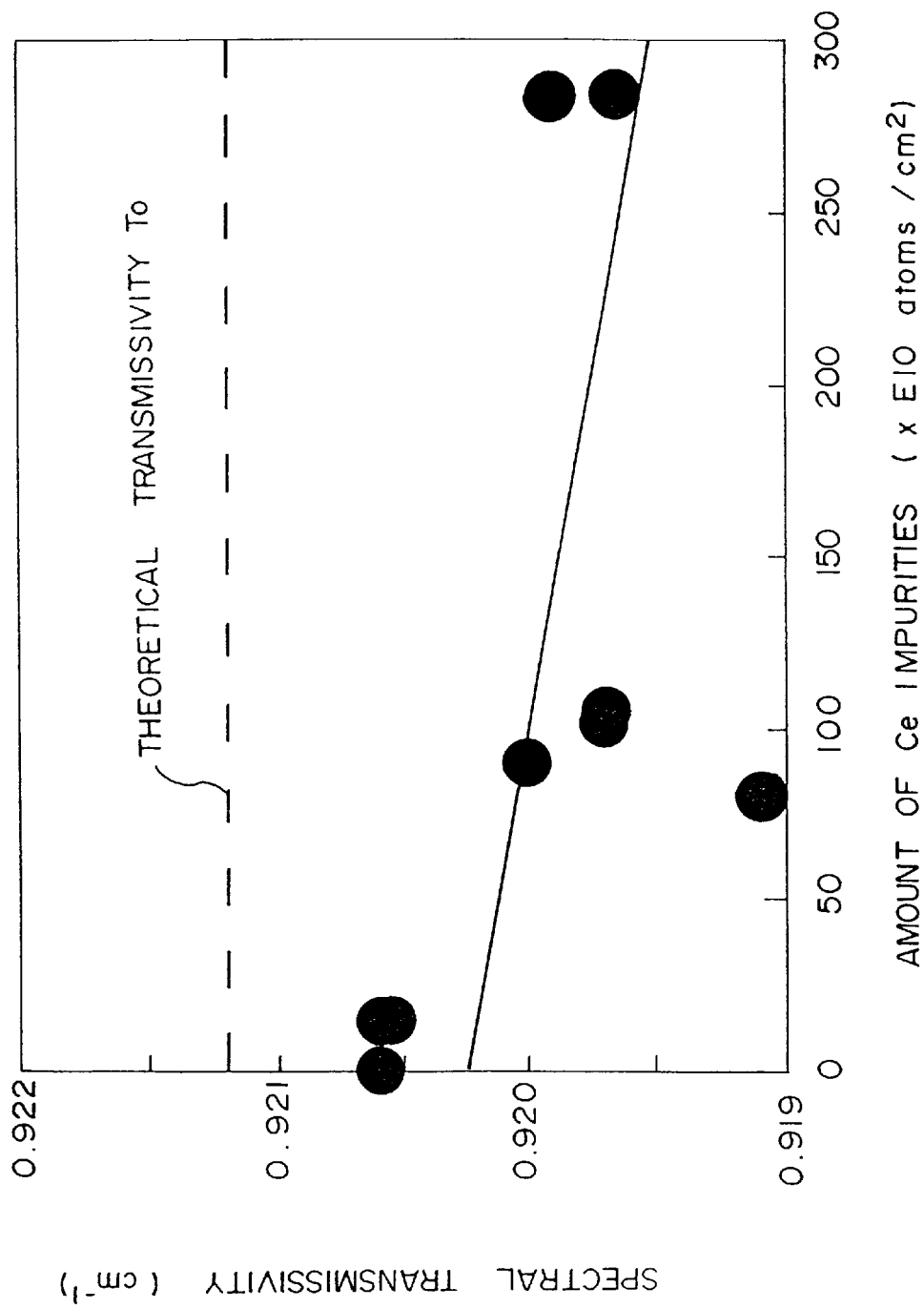
FIG. 3 is a graph plotting the relationship between the amount of residual $CeO_2$ impurities and the spectral transmittance (248 nm).

FIG. 3 shows a relationship between the amount of residual Ce impurities and the spectral transmittance at 248 nm. As shown by this drawing, surface loss is greater in the sample having a larger amount of residual Ce impurities.

This seems to be due to the fact that $CeO_2$, which is a main ingredient of the abrasive agent used when making the sample, remains in minute cracks on the surface of the sample. As the impurities remaining on the surface of the sample, there may be various ingredients contained in the abrasive agent in addition to $CeO_2$, $Al_2O_3$, and $ZrO_2$, which are main ingredients of the abrasive agent for optical materials, as well as diamond grinder particles and the like. Surface loss similar to that noted above may be caused when these ingredients remain on the surface of the sample as a very small quantity of impurities.

Also, at a further shorter wavelength region, the results of b) seem to be obtained as the influence of organic residue having an amount smaller than the limit of detection or the impurities other than Ce or the influence of the structural defects resulting from the residual stress increases for the reason not elucidated yet.

In view of these facts, it has become clear that, as a factor influencing the measurement of transmittance other than surface scattering of the sample, the influence of loss caused by the absorption on the surface of the sample is great.

Therefore, in the method of measuring the transmittance of optical materials, the inventors have studied the method of making a sample for measuring transmittance by which an internal absorption coefficient of 0.001 $cm^{-1}$ can accurately be measured as a significant difference. As a result, it has been found out that the following points are effective:

(A) As optical polishing for making the sample, after prepolishing the sample with a commercial abrasive agent, polishing it with an $SiO_2$ abrasive agent so as to attain a surface roughness rms of 10 Å or less (B) After prepolishing the sample with a normal optical polishing technique, treating the surface of the sample with an acid or alkali several hours before its transmittance is measured.

In (A), since $CeO_2$ itself, which is generally used as a commercial abrasive agent, tends to remain as impurities and causes the transmittance to decrease, the abrasive agent should preferably include ingredients which are hard to remain or do not cause surface absorption even when they remain. In this respect, an abrasive agent mainly composed of fine $SiO_2$ particles, from which grinder particles and abrasive agents with a high purity can be obtained, is effective. However, when only the $SiO_2$ abrasive agent is used for polishing, the polishing speed becomes slow and the working efficiency decreases. When only the finish polishing is effected with the $SiO_2$ abrasive agent, on the other hand, the residual impurities on the surface can effectively be removed while maintaining a desirable working efficiency.

Like (A), the residual impurities on the surface of the sample can be removed in (B). In addition, it is expected that minute cracks may be removed and residual stress may be alleviated to eliminate structural defects. Accordingly, (A) and (B) may be combined together to further improve the accuracy in measurement.

From FIG. 3, the amount of residual Ce impurities where the internal absorption coefficient becomes 0.001 $cm^{-1}$ is estimated as $4 \times 10^{12}$ atoms/$cm^2$. Accordingly, the amount of residual Ce impurities in the sample for measuring the transmittance should be $4 \times 10^{12}$ atoms/$cm^2$ or less.

When the amount of Ce impurities is zero, the difference between the theoretical transmittance value and the spectral transmittance is about 0.001 $cm^{-1}$. This difference seems to be mainly attributable to residual stress. Accordingly, the sample for measuring the transmittance should preferably be free from residual stress.

As means for the acid or alkali treatment, an acid treatment solution such as HF, $HNO_3$, or mixed $HF+H_2SO_4$ solution, an alkali treatment solution such as aqueous $NH_4OH$ solution, or a technique for exposing the sample to an acid or alkali atmosphere may be used.

Various conditions for the acid or alkali surface treatment of the sample, e.g. the concentration of the aqueous solution, temperature, and time of treatment, can voluntarily be set in view of the chemical durability of the sample. It is desirable, however, for the surface treatment here to attain an erosion depth in the order of about 0.01–0.1 µm and a surface roughness rms of not more than 10 Å.

The surface treatment of (B) is effected several hours before the measurement since it has experimentally been proved that the surface loss increases when the sample is left for a long time. Though not elucidated yet, this seems to be attributable to a factor which is similar to a chemical deterioration on the surface of the sample called "burning." Also, attention should sufficiently be paid to the cleaning and drying of the sample after the acid or alkali treatment so as not to cause any chemical deterioration.

Among the acid treatment means, the HF treatment is particularly effective in removing the residual impurities since its aqueous solution with a high purity can easily be obtained. In this case, a very small quantity of F remains on the surface of the sample after the treatment. This remaining F can be detected as Si-F or Si-O-F by ESCA or SIMS (secondary ion mass spectrometer). it is desirable for the sample for measuring transmittance to have a very small quantity of F to be detected while containing no other impurities. Of course, the crystal or optical glass containing F as its composition should be handled in a different way.

The effect obtained by the method of making the sample in accordance with the present invention will be examined while synthetic silica glass is used as an example.

Usually, when a minute absorption of transmittance is to be evaluated, the dependence of the transmittance upon the thickness of the sample is measured and the absorption coefficient, a $cm^{-1}$, is calculated.

Figure 4:
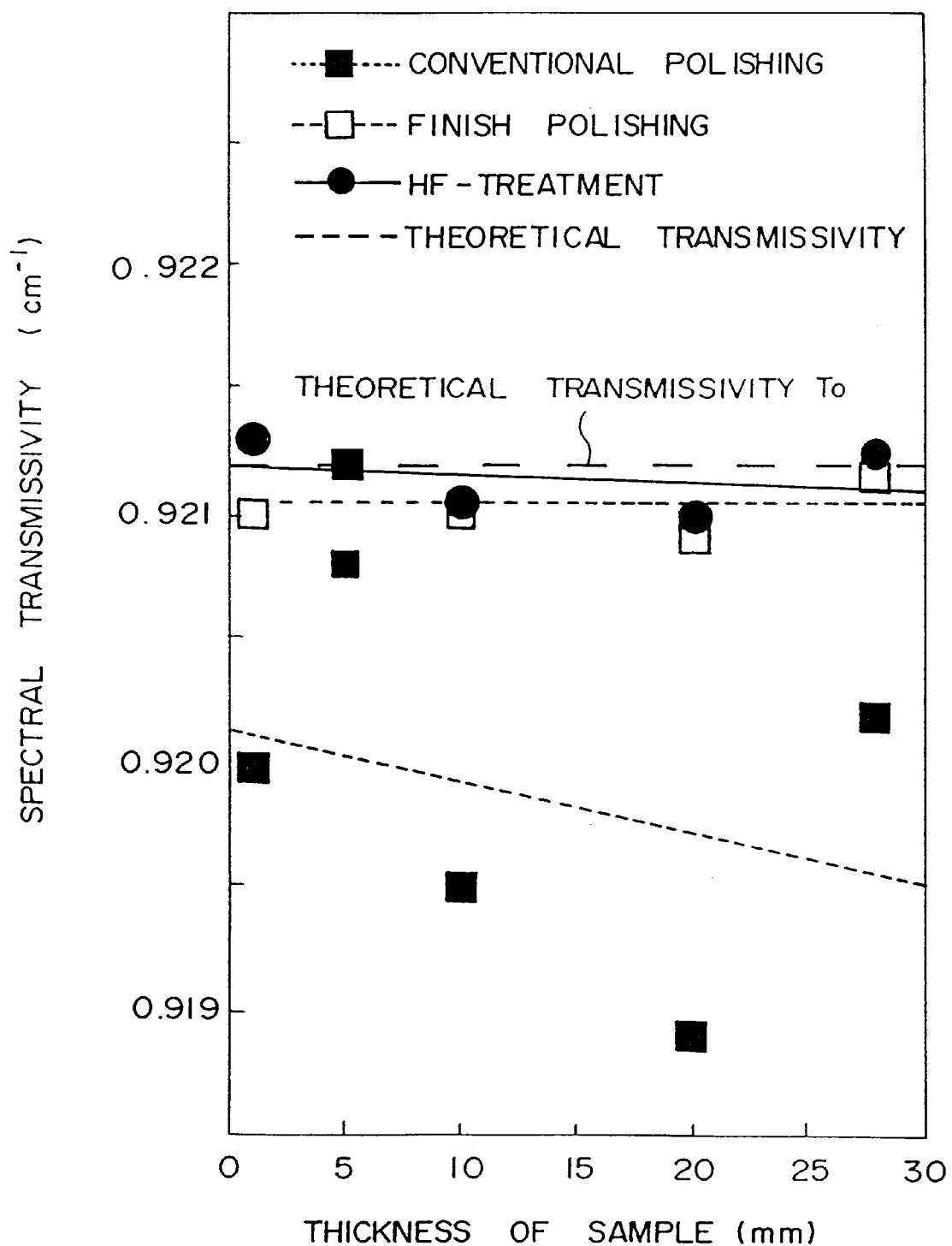
FIG. 4 is a graph showing the behavior of the spectral transmittance (248 nm) with reference to methods of making the sample.
Figure 5:
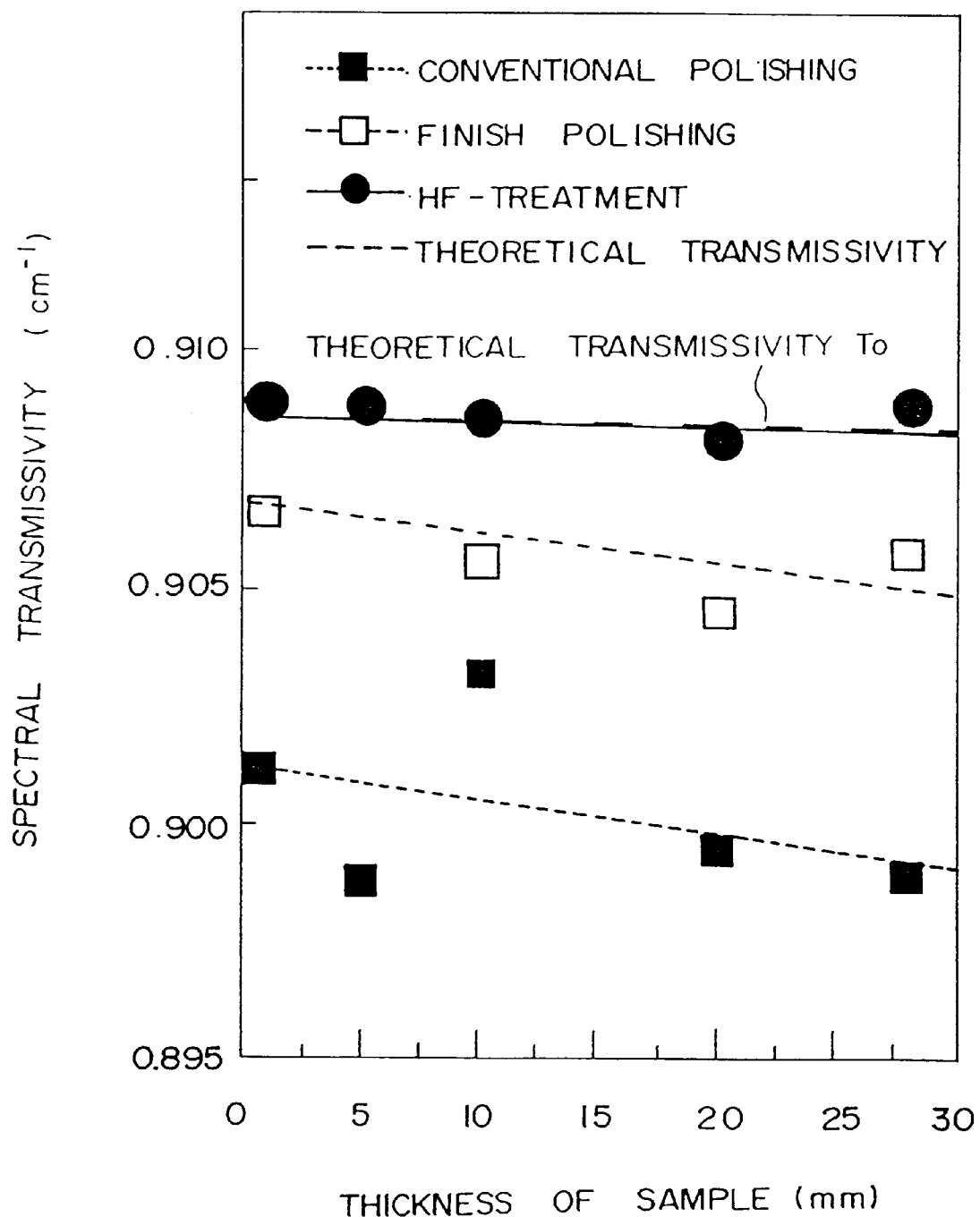
FIG. 5 is a graph showing the behavior of the spectral transmittance (193 nm) with reference to methods of making the sample.

Accordingly, the spectral transmittance with respect to the thickness of the sample was measured at measuring wavelengths of 248 nm and 193 nm. Its results are shown in FIGS. 4 and 5.

The sample was made to have, as a standard, a parallelism of 30 seconds or less, a surface accuracy in the same order as the parallelism or less, and a surface roughness rms of 10 Å or less.

In the first place, the optical polishing surface was subjected to finish polishing with an $SiO_2$ abrasive agent and then its spectral transmittance was measured.

Further, the same sample was immersed in a 10% aqueous HF solution at about 20° C. for about 1 minute to effect a surface treatment and then its spectral transmittance was similarly measured. AFM (atomic force microscope) inspection confirmed that the HF treatment of the sample had yielded an erosion death of about 0.08 µm and had not deteriorated but slightly improved the surface roughness.

As shown in FIG. 4, at the measuring wavelength of 248 nm, the spectral transmittance of the sample finished with the $SiO_2$ abrasive agent substantially coincides with the theoretical transmittance. Also, similar results were obtained when the sample was treated with HF.

At the measuring wavelength of 193 nm shown in FIG. 5, while the finish polishing with the $SiO_2$ abrasive agent effectively reduced the surface loss of the conventional polishing, the resulting spectral transmittance failed to coincide with the theoretical transmittance. When the sample was treated with HF, its result of measurement coincided with the theoretical transmittance.

Therefore, as a method of making a sample for measuring the transmittance of optical materials, it is effective to conduct a finish polishing step with an $SiO_2$ abrasive agent as well as an acid or alkali treatment step. In particular, at 300 nm or less, both steps can be combined together to further increase the accuracy in measurement.

EXPERIMENT 1

The above-mentioned silica glass piece 1b was cut out from the ingot 1 as a sample for evaluating the accuracy in measurement of transmittance obtained by the present invention and for comparing the measured value with the theoretical transmittance.

The used method of measuring the internal transmittance of the silica glass having a high purity comprises the steps of preparing 5 pieces each of 5 kinds of samples with different thickness values, measuring their spectral transmittance values at 248 nm and 193 nm, and calculating the internal transmittance from the measured values (cf. Japanese Patent Application No. 5-211217). The form of the sample and conditions for making the same are as follows:

Form: $\Phi 60 \times t1, 5, 10, 20, 28 \pm 0.01$ mm

Number: 5 pieces for each thickness value

Surface Accuracy: $3\lambda$ ($\lambda=546$ nm)

Parallelism: 10 seconds

Surface roughness: rms 2 Å

Finish polishing: fine $SiO_2$ particle

Acid treatment: 10% aqueous HF solution (20° C., 1 minute)

Figure 6:
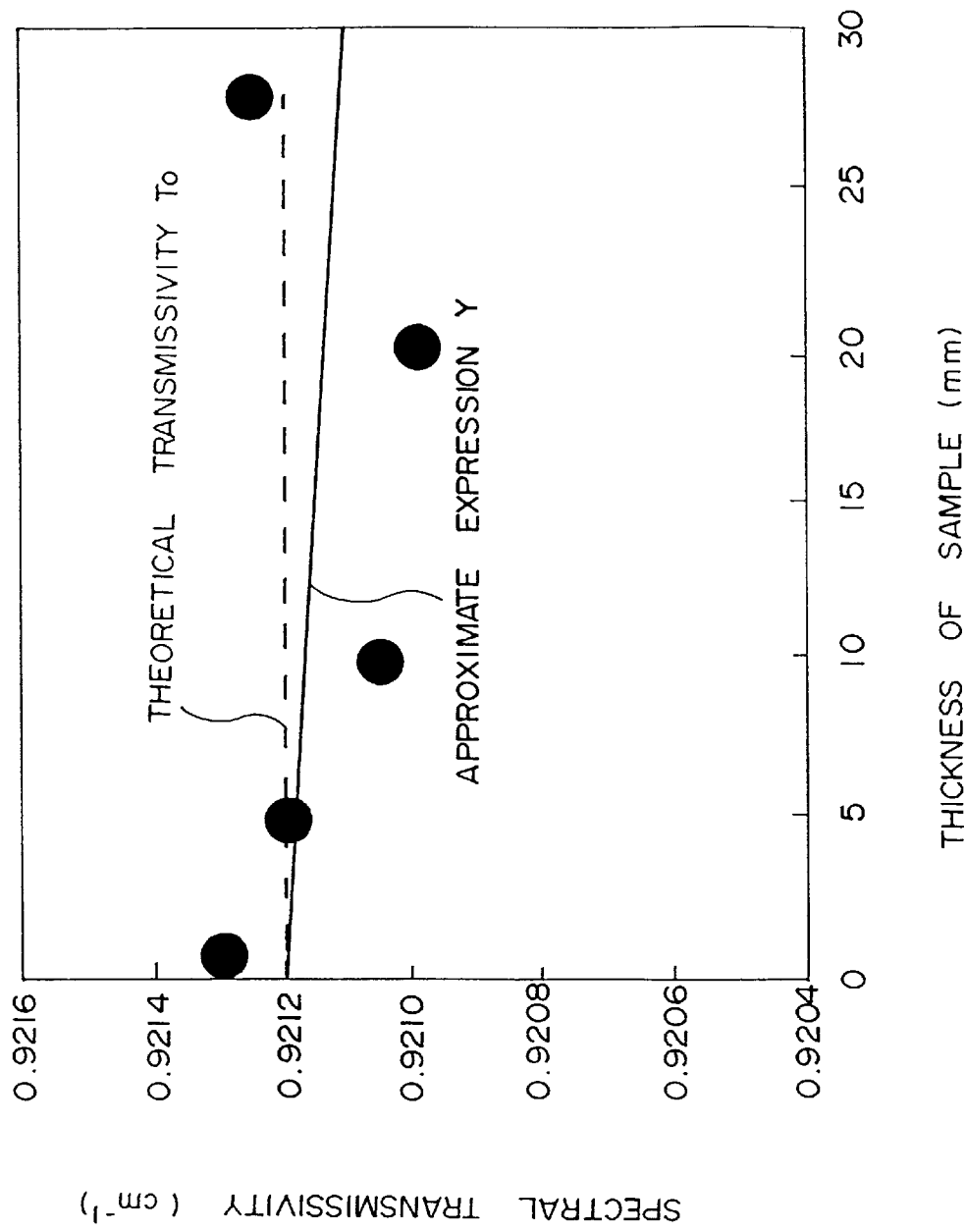
FIG. 6 is a graph plotting the results of measurement of the 248 nm spectral transmittance of the synthetic silica glass in accordance with EXPERIMENT 1 of the present invention.
Figure 7:
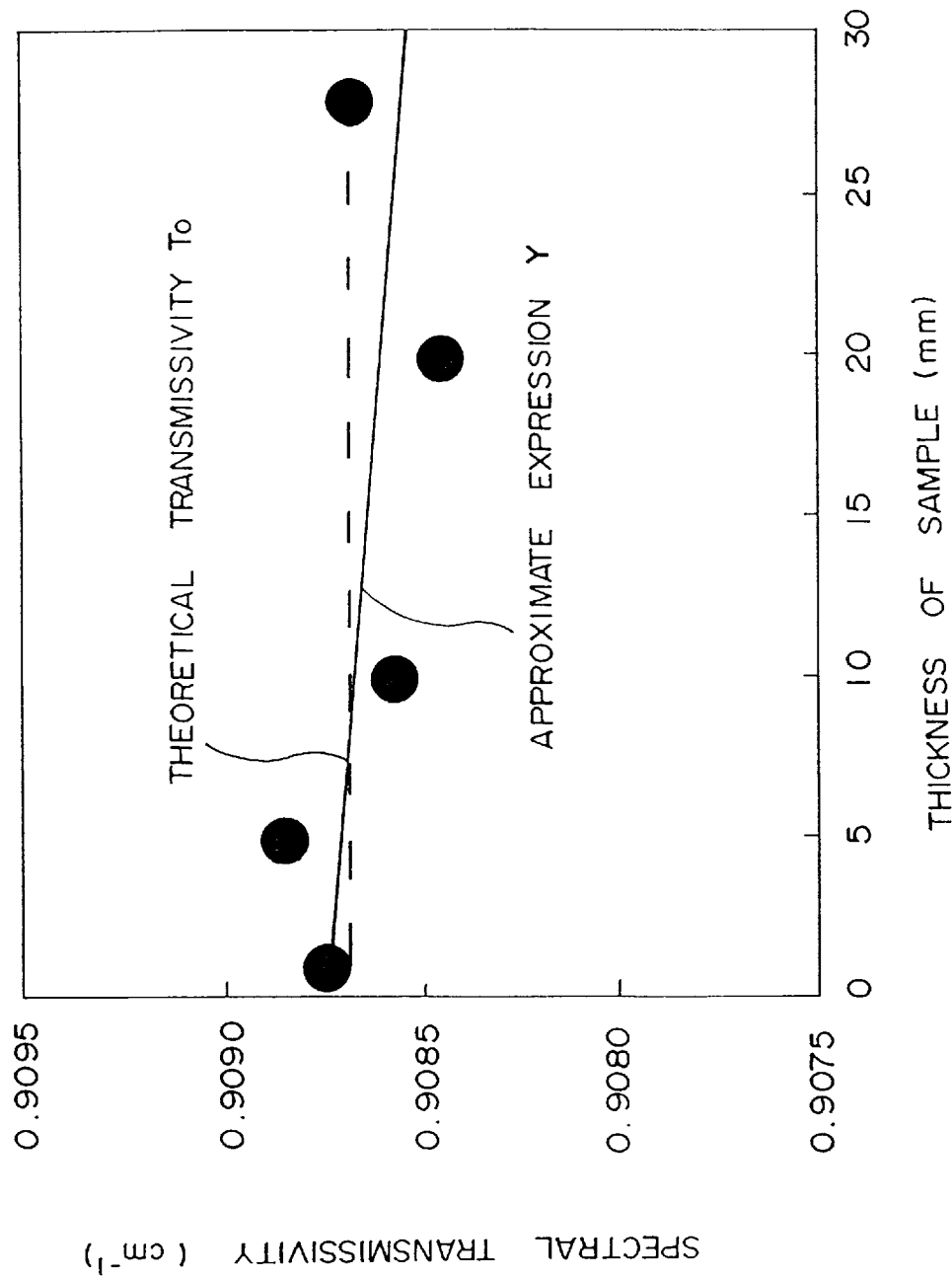
FIG. 7 is a graph plotting the results of measurement of the 193 nm spectral transmittance of the synthetic silica glass in accordance with EXPERIMENT 1 of the present invention.

Each of FIGS. 6 and 7, in which the results of measurement are plotted, has x-axis for thickness and y-axis for the transmittance including reflection loss.

The average of the measured values for each thickness has been calculated and plotted. Also, the average at each thickness is approximated by a line.

The repeated reproducibility levels of the measured values, in which the levels of accuracy in the spectrophotometer and sample have been taken into account, are within the ranges of $\pm 0.0001$ cm$^{-1}$ and $\pm 0.0005$ cm$^{-1}$ at the measuring wavelengths of 248 nm and 193 nm, respectively.

1) At the measuring wavelength of 248 nm, the approximate expression is obtained from FIG. 6 as follows:

$$Y=0.921197-3.08\times 10^{-6}X$$

The transmittance value including the reflection loss at 10 mm-thickness was obtained by this equation and the 10 m-internal transmittance value at 248 nm was calculated in accordance with the following equations:

10 mm-transmittance including reflection loss =0.921166 cm$^{-1}$ wherein:

theoretical transmittance=0.921166 cm$^{-1}$ 10 mm-internal transmittance=0.921166/0.921194= 0.99997 cm$^{-1}$ 2) At the measuring wavelength of 193 nm, the approximate expression is obtained from FIG. 7 as follows:

$$Y=0.908751-7.13\times 10^{-6}X$$

As in the case with 1), the 10 mm-internal transmittance value at 193 nm was calculated as follows:

10 mm-transmittance including reflection loss 0.908680 cm$^{-1}$ wherein:

theoretical transmittance=0.908734 cm$^{-1}$ 10 mm-internal transmittance=0.908680/0.908734= 0.99884 cm$^{-1}$ These results show that, when the standard for the sample and method of making the same in accordance with the present invention are used, repeated reproducibility of the transmittance including reflection loss is obtained at 248 nm and 193 nm with differences between their transmittance values and the theoretical transmittance of $2.8\times 10^{-5}$ cm$^{-1}$ and $5.4\times 10^{-5}$ cm$^{-1}$, respectively, which yield an accuracy in measurement which is sufficient for studying an internal absorption coefficient of 0.001 cm$^{-1}$.

Also, it is understood that this sample has an internal transmittance of 0.999 cm$^{-1}$ or more. Further, when its internal absorption loss is taken into account, it is considered that there is substantially no internal absorption in practice.

When the surface of the sample was analyzed with the total reflection X-ray fluorescence method, Ce impurities were not more than the limit of detection. Further, a very small amount of F was detected upon its measurement.

Since the silica glass evaluated this time has a high quality, its internal absorption is very small. However, the absorption in the order of 0.001–0.005 cm$^{-1}$, which is caused by reductants of $SiO_2$, Na impurities, or the like, may sometimes be observed in those with a low quality at about 200 nm to the shorter wavelength region. While the quality has conventionally been evaluated with the internal absorption in such an order, smaller differences in the quality can be detected in accordance with the present invention.

EXPERIMENT 2

Silica glass samples with different qualities were used to obtain transmission spectra including reflection loss in the wavelength region of 185–260 nm. A spectrophotometer, whose optical axis had been adjusted such that the deviation of the spectral transmittance from the theoretical transmittance accompanying the increase in the thickness of the sample was within the range of $\pm 0.0001$ cm$^{-1}$ or less when the spectral transmittance at 365 nm was measured, was used for the measurement (cf. Japanese Patent Application No. 5-211217). The form of the sample and conditions for making the same are as follows:

Type: A (high purity), B (general), C (general)

Form: $\Phi 60 \times 10 \pm 0.01$ mm

Number: 1 piece each

Surface Accuracy: $3\lambda$($\lambda=546$ nm)

Parallelism: 20 seconds

Surface roughness: rms 8 Å

Finish polishing: none

Acid treatment: 10% aqueous HF solution (20° C., 1 minute)

Figure 8:
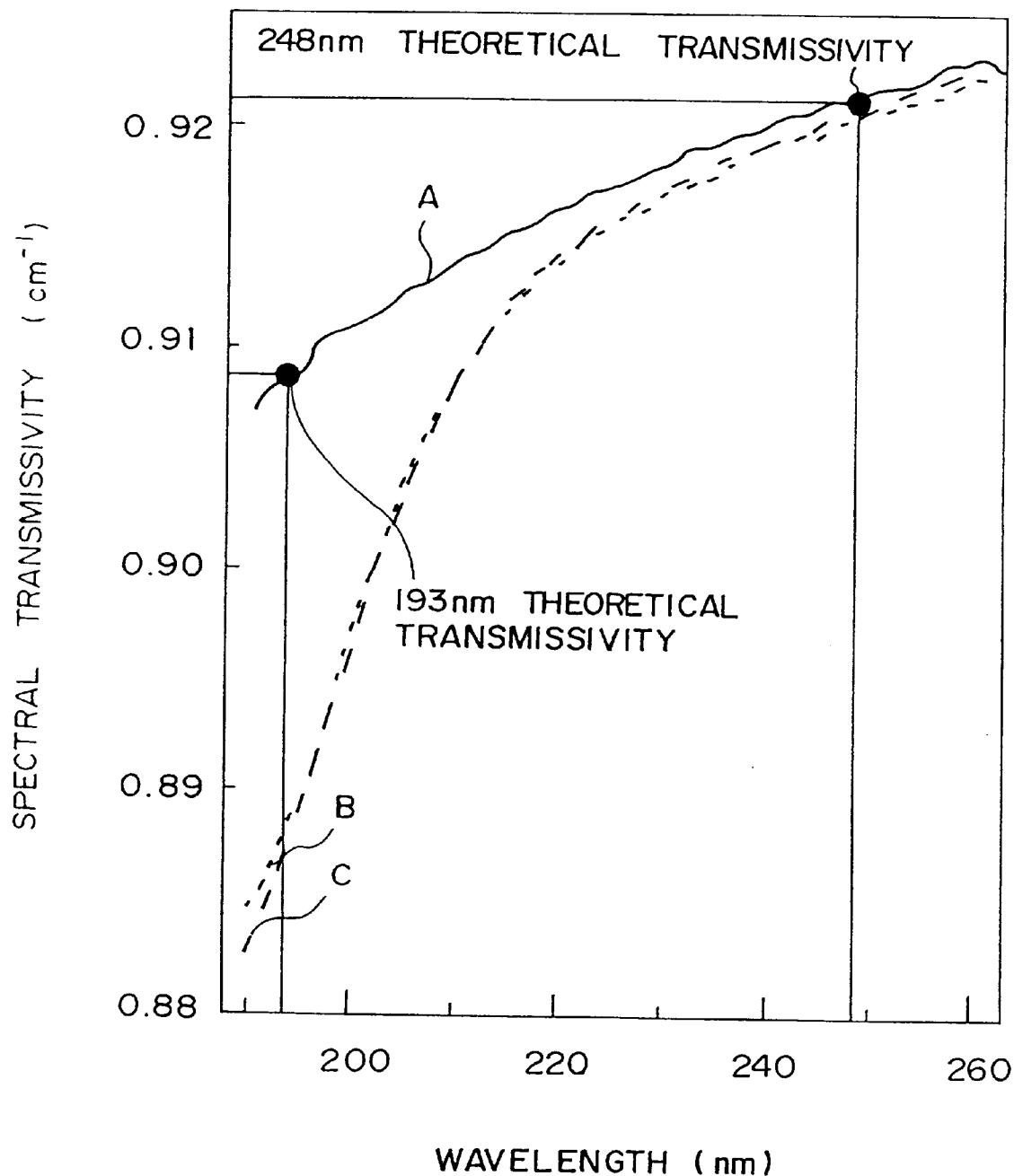
FIG. 8 is a graph comparatively showing the spectral transmittance values of the synthetic silica glass in accordance with EXPERIMENT 2 of the present invention with reference to its qualities.

The results of measurement is shown in FIG. 8 in which the wavelength and the transmittance including reflection loss are respectively indicated at x-axis and y-axis. As shown in this drawing, the results have proved that sample A containing several ppb of metal impurities substantially coincides with the theoretical transmittance at the measuring wavelengths of 248 nm and 193 nm within an error level of 0.1 % or less, while samples B and C containing several ten to several hundred metal impurities do not coincide with the theoretical transmittance, thereby indicating that there is internal absorption in the silica glass of the sample.

Also, as the transmittance continuously changes with respect to the measuring wavelength, it is understood that the surface of the sample thus manufactured is stable regardless of the wavelength and sufficiently satisfies the measuring accuracy at the measuring wavelength region of 250 nm or less.

In view of the foregoing, it can be judged that, while silica samples B and C satisfy the standard of 10 mm-internal transmittance of 0.999 cm$^{-1}$ or more as a lens material for KrF excimer laser steppers, they cannot satisfy the standard for ArF excimer lasers. Also, designed performance of the stepper is expected to deteriorate when such materials as B and C are used.

EXPERIMENT 3

Figure 21:
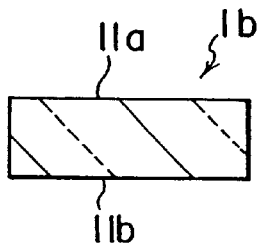
FIG. 21 shows a sample which has been made from an ingot of fluorite in the same manner as noted above.

FIG. 21 shows a sample 1b which has been made from an ingot of fluorite. This sample is made in the same process and has the same structure as the silica glass sample except for the materials used.

Bridgman method (also known as Stockberger method or crucible-descending method) was used, while minutely controlling the temperature condition, descending speed, or the like, to cultivate a single crystal of fluorite 1b having a diameter of 250 nm and a height of 300 mm.

Inductively coupled plasma spectrometry quantitatively analyzed that thus obtained silica glass ingot and fluorite single crystal contained 1b ppb or less of each metal impurities (Ti, Cr, Fe, Ni, Cu, Zn, Co, and Mn). Namely, these silica glass and fluorite have a high purity.

The above-mentioned single crystal of fluorite was cut out as a sample and, as in the case with EXPERIMENT 1, its spectral transmittance was measured and evaluated at 248 nm and 193 nm.

Form: Φ60×t, 5, 10, 20, 28±0.01 mm

Number: 5 pieces for each thickness value

Surface Accuracy: 31 (λ=546 nm)

Parallelism: 10 seconds

Surface roughness: rms 2 Å

Finish polishing: fine $SiO_2$ particle

Acid treatment: 0.02N aqueous nitric acid solution (20° C., 1 minute)

Figure 9:
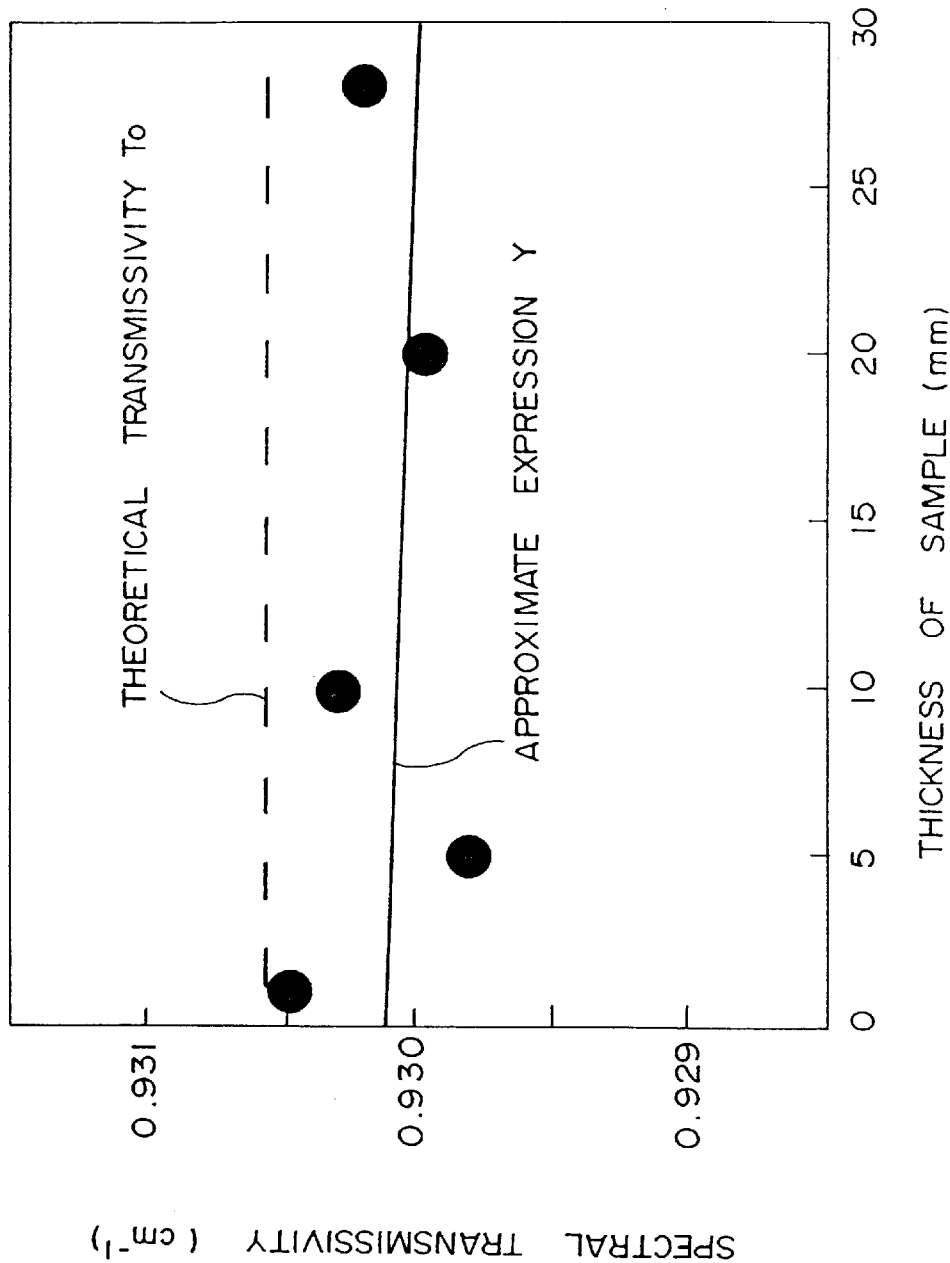
FIG. 9 is a graph plotting the results of measurement of the 248 nm spectral transmittance of fluorite $CaF_2$ in accordance with EXPERIMENT 3 of the present invention.

Each of FIGS. 9 and 10, in which the results of measurement are plotted, has x-axis for thickness and y-axis for the transmittance including the reflection loss. The average of the measured values for each thickness has been calculated and plotted. Also, the average at each thickness is approximated by a line.

The repeated reproducibility levels of the measured values, in which the levels of accuracy in the spectrophotometer and sample have been taken into account, are in the same order as those of EXPERIMENT 1.

1) At the measuring wavelength of 248 nm, the approximate expression is obtained from FIG. 9 as follows:

$$Y=0.930216-4.36\times10^{-6}X$$

The transmittance value including the reflection loss at 10 mm-thickness was obtained by this equation and the 10 mm-internal transmittance value at 248 nm was calculated in accordance with the following equations:

10 mm-transmittance including reflection loss 0.930172 cm$^{-1}$ wherein:

theoretical transmittance =0.930709 cm$^{-1}$ 10 mm-internal transmittance 0.930172/0.930709= 0.99942 cm$^{-1}$ 2) At the measuring wavelength of 193 nm, the approximate expression is obtained from FIG. 10 as follows:

$$Y=0.922458-1.075\times10^{-5}X$$

As in the case with 1), the 10 mm-internal transmittance value at 193 nm was calculated as follows:

10 mm-transmittance including reflection loss =0.922351 cm$^{-1}$ wherein:

theoretical transmittance =0.922858 cm$^{-1}$ 10 mm-internal transmittance=0.922351/0.922858= 0.99945 cm$^{-1}$ From these results, it has been judged that the internal transmittance is 0.999 cm$^{-1}$ or more at both 248 nm and 193 nm. When the internal scattering loss is taken into account, it can be judged that there is substantially no internal absorption in practice. While the CaF, sample evaluated here has such a high purity that only minute internal absorption exists, several kinds of absorption bands may sometimes be observed at visible to ultraviolet region in those with a poor quality. The sample in accordance with the present invention can be used for measuring the transmittance to detect such a minute difference in quality.

When the standard for the sample and method of making the same in accordance with the present invention are used, it has become possible to accurately measure the internal transmittance of optical materials with an error level of ±0.001 cm$^{-1}$ or less. The present invention is effective, in particular, in the measurement of transmittance at a short wavelength region of the ultraviolet region and at the vacuum ultraviolet region.

Also, the present invention can be used for polishing optical components in which minute absorption at the short wavelength region is problematic.

Next, a piece of a preform for an optical component according to a second embodiment will be explained below. Regarding the following piece and the method for fabricating the same, not described is as same as the piece and the method described above.

Figure 22:
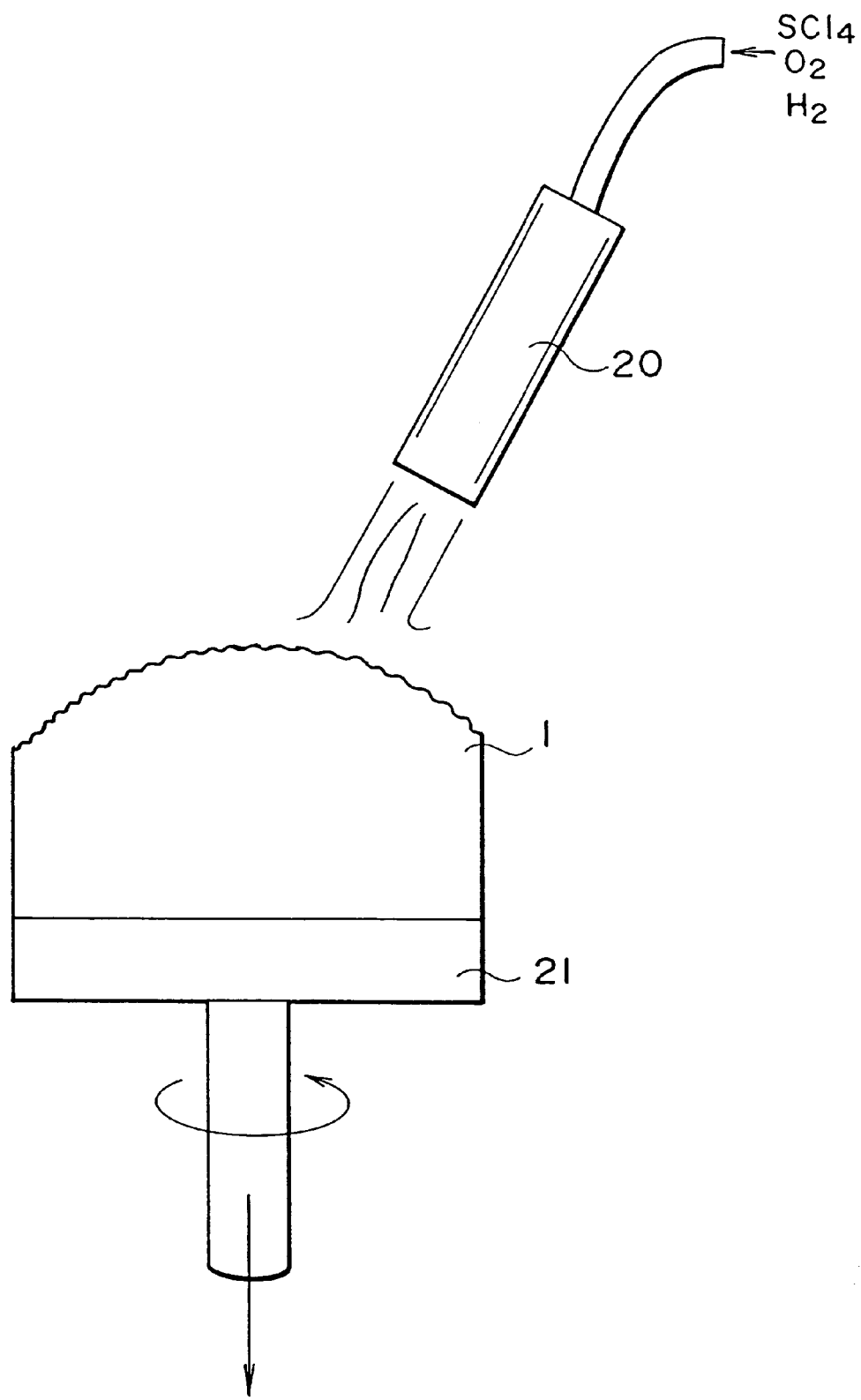
FIG. 22 is a view of a preform and a system for making the preform.
Figure 23:
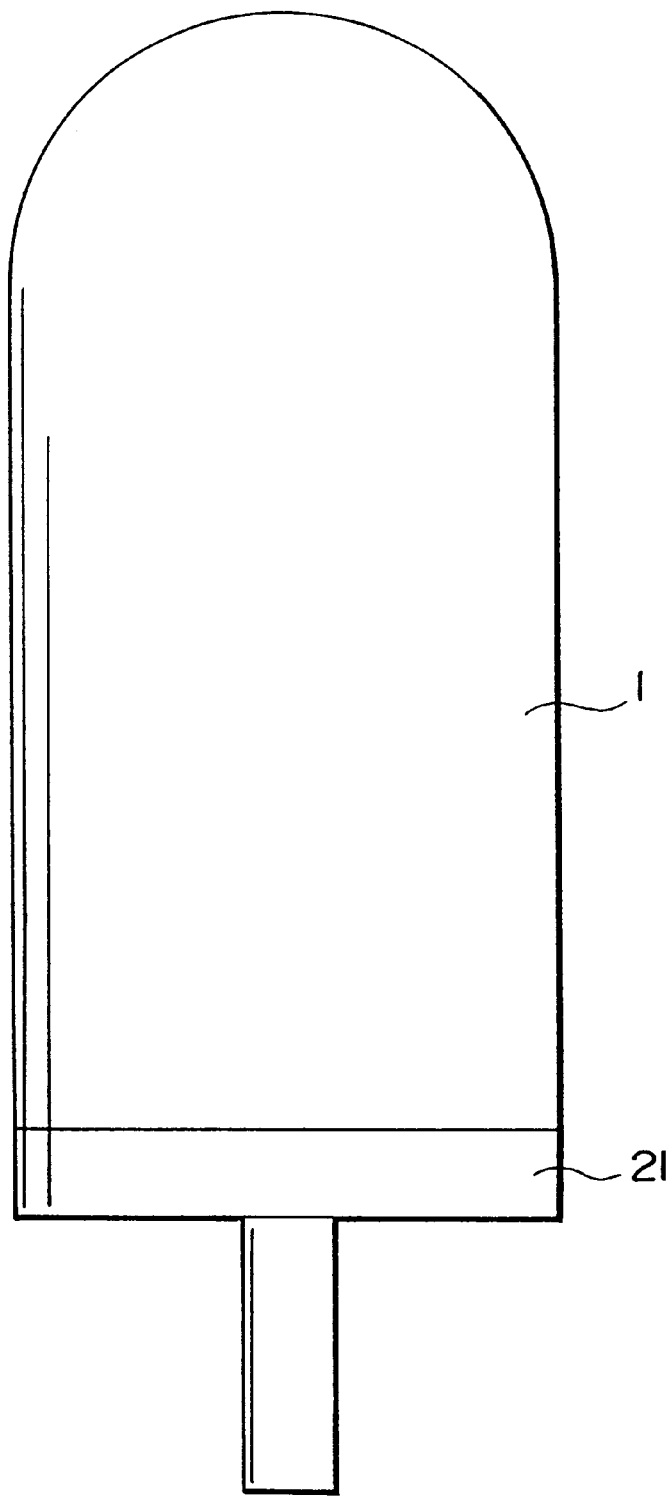
FIG. 23 shows the preform.

The method for making the preform is explained by using FIGS. 22 and 23. The preform is fabricated by using a burner 20. The burner 20 is arranged closer to a SiC substrate 21. $SiCl_4$ gas, $O_2$ gas and $H_2$ gas are introduced into the burner 20, and these gases react each other to form glass particles. The fluid of the glass particles, which is so-called soot, is transmitted to the substrate 21, and the glass particles are deposited on the substrate 21 and melted at the time of colliding the glass particles with the substrate 21. The substrate 21 is rotated while the deposition is performed.

After the deposition, the preform 1 is cooled down to a room temperature. FIG. 23 shows the preform 1 under such a state.

Figure 24:
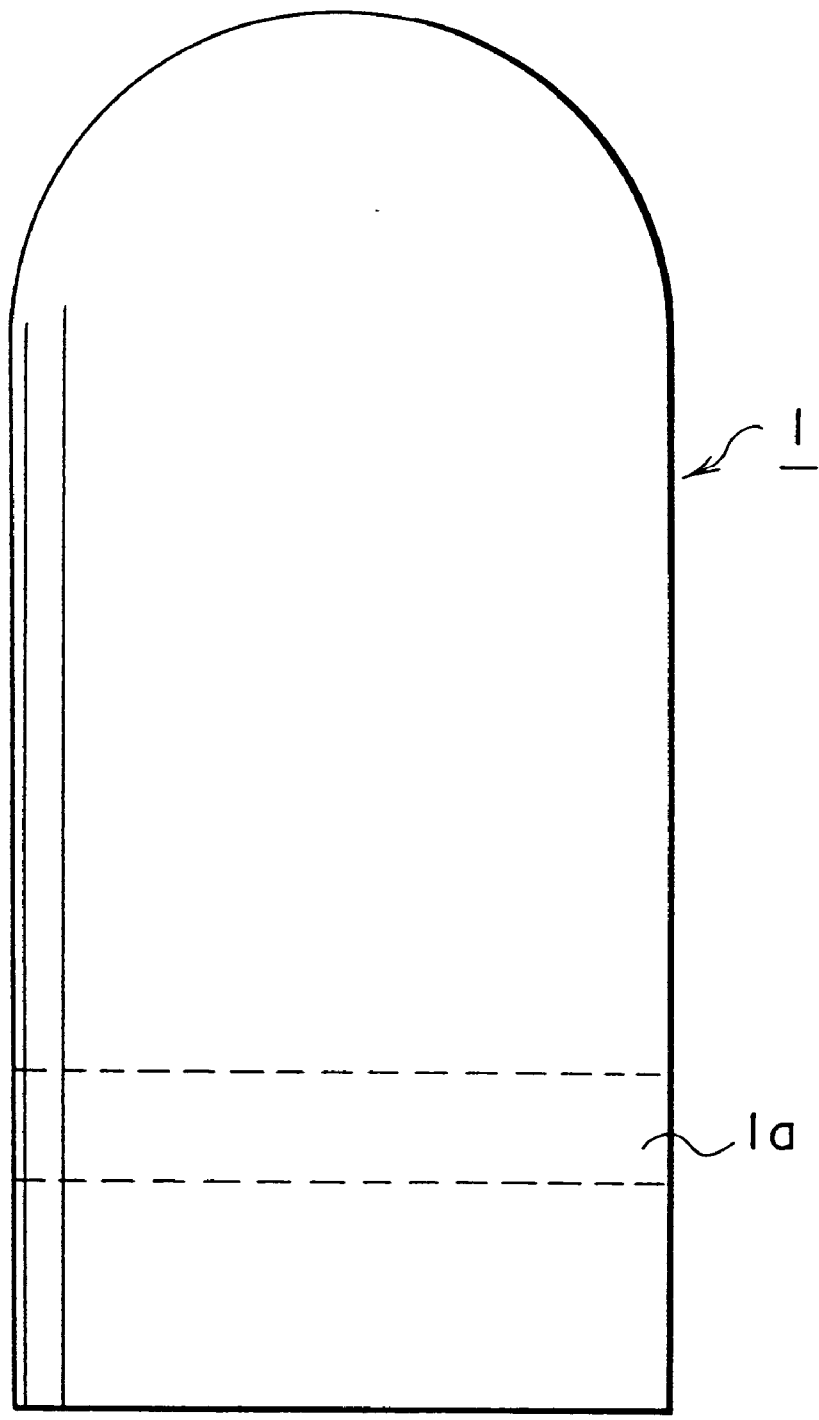
FIG. 24 shows the preform.

The substrate 21 is detached from the preform 1 as shown in FIG. 24. A piece according to the present embodiment is cut out from this preform 1. A method of making the piece for measuring a transparency of the preform 1 is explained below.

First, the piece 1a is cut out from the preform 1 along dotted lines in FIG. 24, by using a diamond saw. Each of the dotted lines is perpendicular to the axis of the preform 1.

Figure 25:
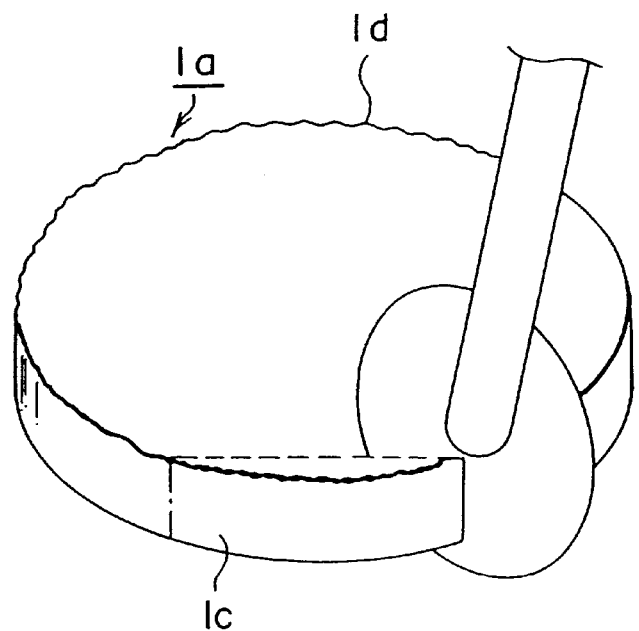
FIG. 25 shows a way of cutting a glass piece which has been cut out from the glass ingot of FIG. 24.

Second, a sub niece 1c near its periphery is cut from a main piece 1d of the piece 1a by using a diamond saw 2 as shown in FIG. 25.

Figure 26:
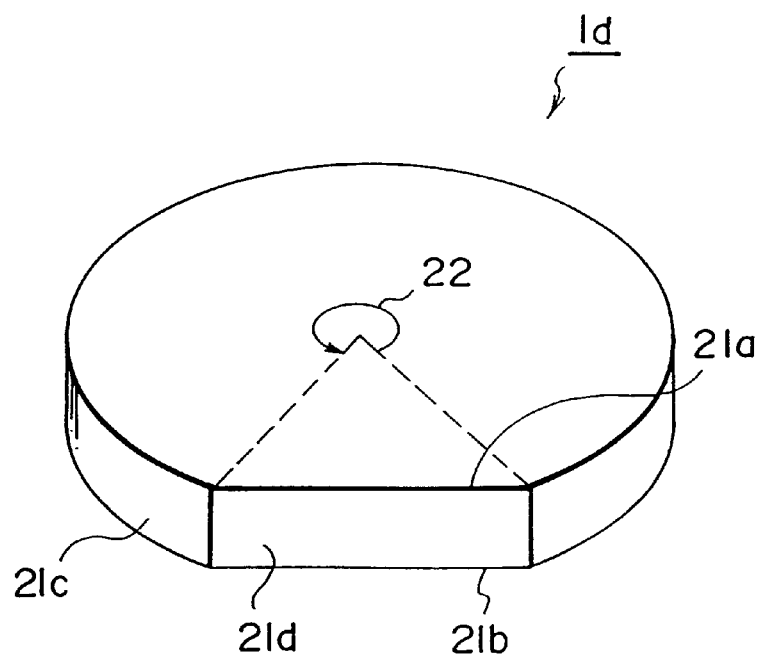
FIG. 26 shows a glass piece.

Third, the surfaces of the piece 1d is treated as same as be the surfaces of the piece 1b, except its drying step. That is, the piece 1d is taken out from the container 9 shown in FIG. 18 and dried while being supported by its corners alone. A special holder having a plurality of members 210 is used for supporting the piece 1d. FIG. 26 shows the piece after this treatment.

This piece 1d has a front surface 21a and a back surface 21b. The angle between the surfaces 21a and 21b is less than 30 seconds, and the surfaces 21a and 21b are substantially flat. The piece 1d has side surfaces 21c and 21d connecting the front surface 21a to the back surface 21b. One 21c of the side surfaces is curved round, and the other 21d is flat. The side surface 21c is almost cylindric and the angle 22 at the circumference of the side surface 21c is larger than 270°.

Figure 27:
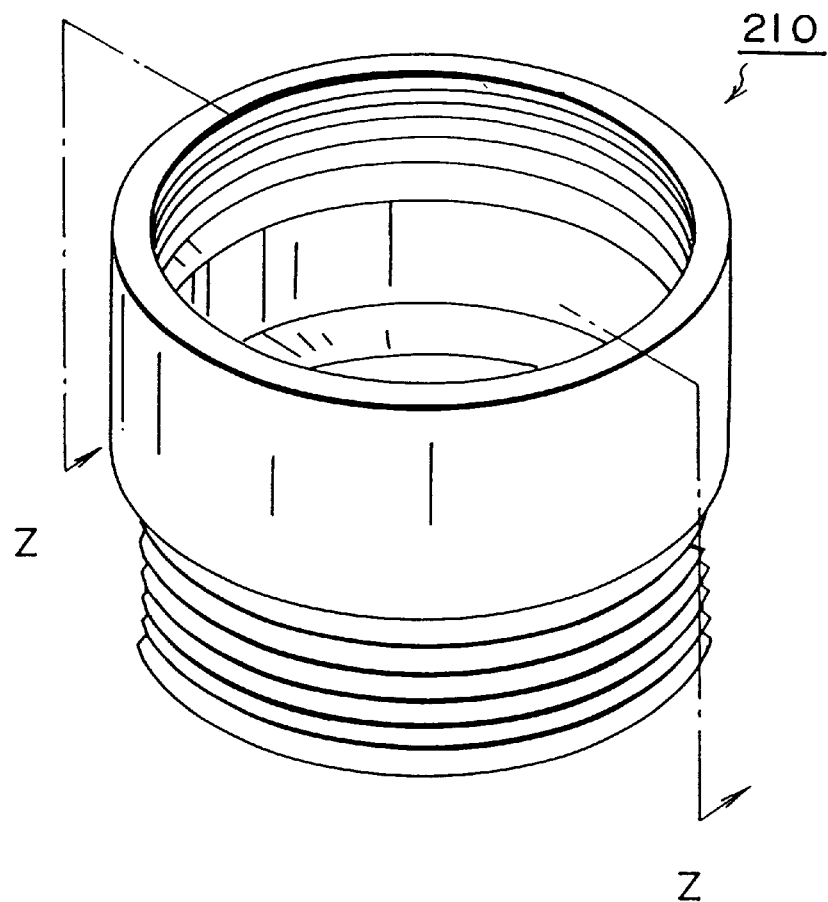
FIG. 27 shows a member of a holder.
Figure 28:
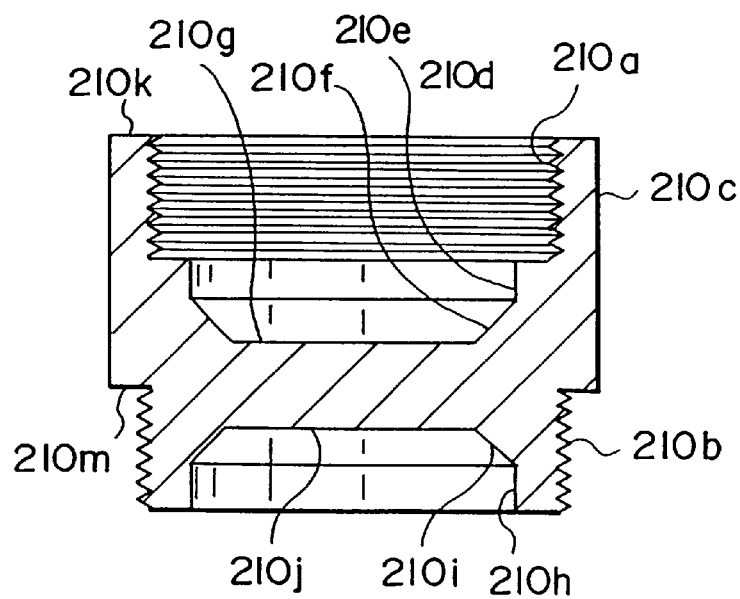
FIG. 28 shows a cross sectional view of the member of FIG. 27.

FIG. 27 shows a perspective view of a member 210 of the holder, and FIG. 28 is a cross-sectional view of the member 210 taken along the line Z—Z of FIG. 27.

The member 210 has a cylindrical outer surface 210c, and an outer thread part 210b continued to the outer surface 210c via a lower lip 210m. The diameter of the cylindrical outer surface 210c is greater than that of the thread part 210b. The member 210 has an inner threaded portion 210a opposing to the outer surface 210c, and an inner cylindrical surface 210e connected the inner thread portion 210a via an inner lip 210d. An inner conical surface 210f is continued to the inner cylindrical surface 210f, and a circular bottom surface 210g crosses the conical surface 210f at an obtuse angle. The upper inner surfaces forms an upper cavity of the member 210. The member 210 has a lower cavity which in arranged under the upper cavity. The lower cavity is formed by a lower cylindrical inner surface 210h opposing to the outer thread part 210b, a lower conical surface 210i continued to the lower cylindrical inner surface 210h and a circular ceiling 210j which crosses the conical surface 210i at obtuse angle.

Figure 29:
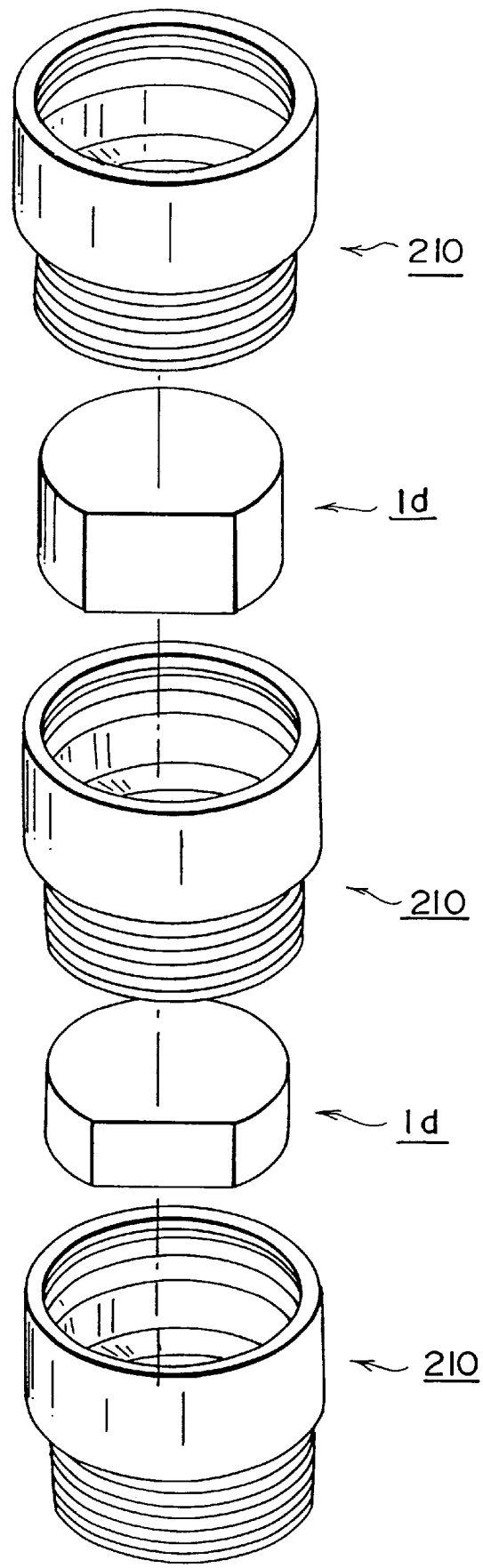
FIG. 29 shows the holder and the pieces.
Figure 30:
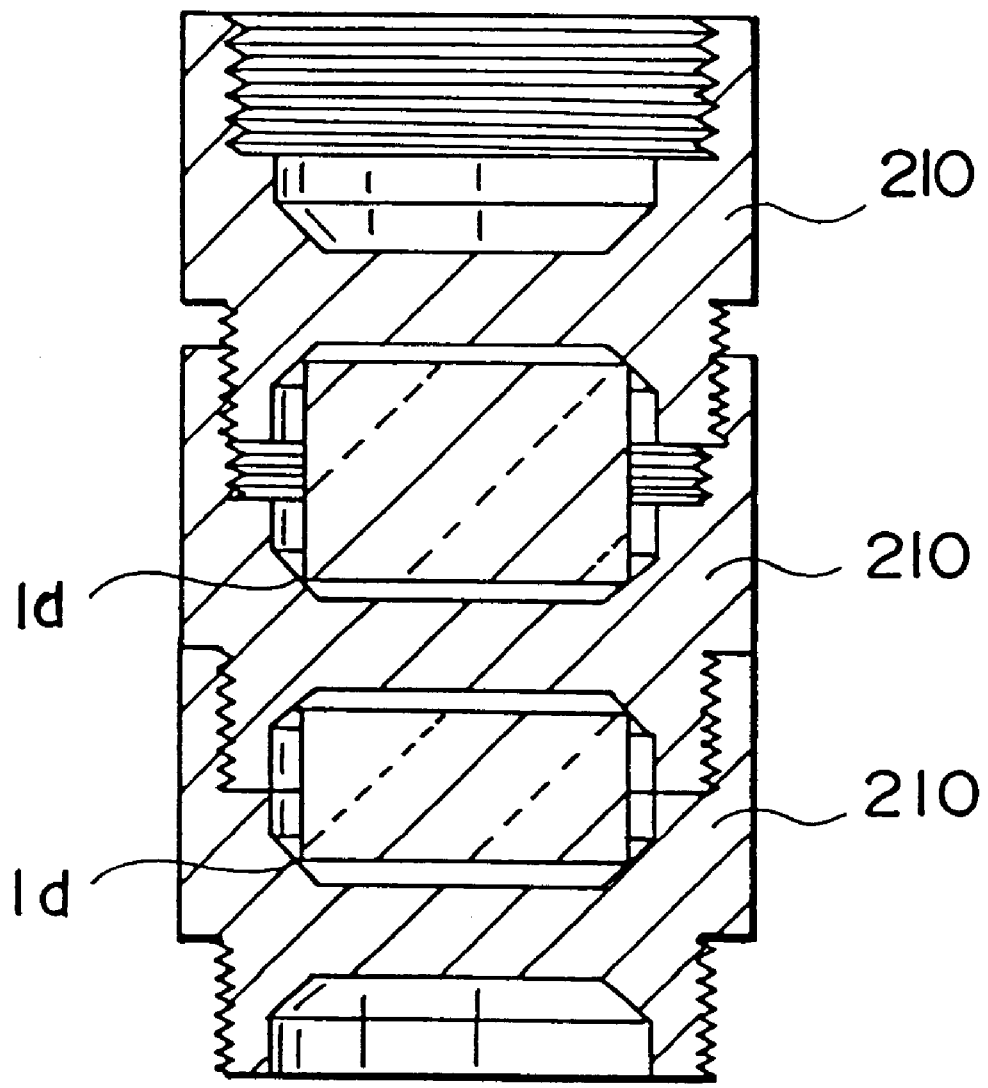
FIG. 30 shows a cross sectional view of the combined holder.
Figure 31:
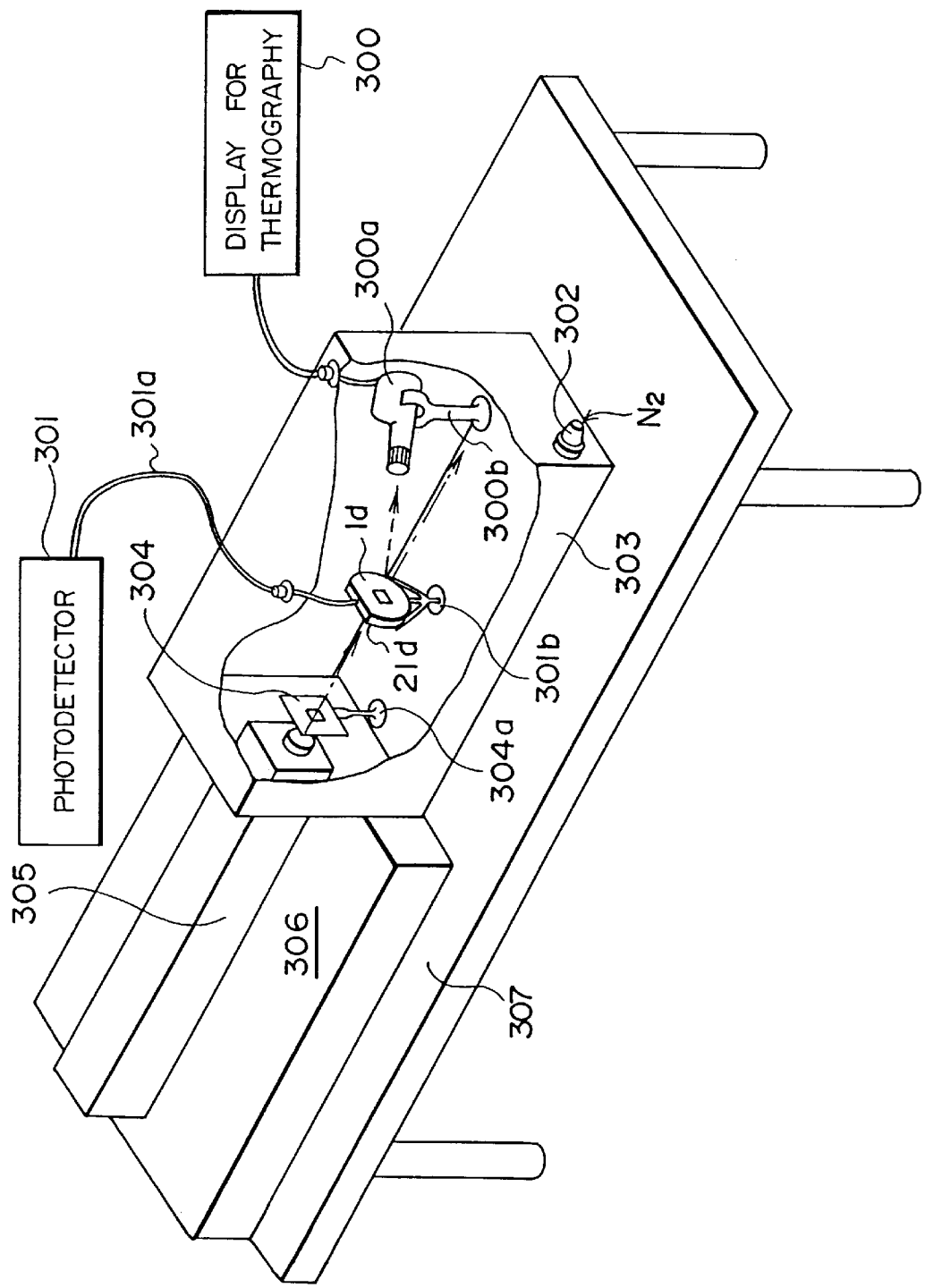
FIG. 31 shows a measuring system.

The holder consisting of a plurality of members 210 are shown in FIGS. 29 and 30. Three members 210 and two pieces sandwiched by the members 210 are shown in FIGS. 29 and 30, and terms of "upper", "middle" and "lower" are used based on the drawings. The members 210 are combined by fastening each of the outer thread surfaces 210b to each of the inner thread surfaces 210a. When these members 210 are combined together, the cross section of the holder has an opening AP which is almost in an octagon shape. Nevertheless the thickness of the upper piece 1d is thicker than that of the lower piece 1d, the holder can hold both of the pieces 1d as shown in FIGS. 29 and 30. The piece 1d is supported by the conical surfaces 210f and 210i alone, thereby the member 210 is dried while the surfaces 21a, 21b, 21c and 21d are not in contact with the holder.

The piece 1d is evaluated by using a system shown in FIG. 30. This system has an excimer laser light source 305 such as a KrF excimer laser, a photo-mask 304 arranged in a pass way of the light, and an infrared camera 300a for picking up an infrared image of the piece 1d. The laser light source 305 is mounted on a table 307 via a spacer 306. The photo-mask 304 is supported by a holder 304a, the piece 1d is supported by the a holder 301b and the camera 300a is supported by a holder 300b. All of the devices 304, 304a, 301b, 300a and 300b are arranged in a box such as a desiccator 303. The box 303 is filled with nitrogen gas. The gas is introduced into the desiccator 303 via a cock 302.

After the piece 1d is fixed to the holder 301d, the evaluation is performed. The excimer laser light source 305 emits a laser light beam, and the light passes through the photo-mask 304 and is emitted onto the niece 1d. The infrared image of the piece 1d is detected by the IR camera 300a. The data of the infrared image detected by the IR camera 300a is corresponding to the temperature distribution in the piece 1d, and the temperature distribution is detected by a thermograph (Thermo Traser, NEC San-ei, type 6T62) using the IR camera 300a. The temperature distribution image is displayed on the display 300. Since the piece 1d has a circular shape, the temperature distribution in the piece 1d becomes uniform.

When the laser light is emitted onto the piece 1d, photoluminescence is occurred in the piece 1d. The luminescence is emitted through the flat side surface 21d. An optical fiber 301a is optically coupled to the flat side surface 21d, and the luminescence is introduced into a spectrophotometer 301 (Ohtsuka Electronics, type IMUC7000) via the fiber 301a.

Figure 32:
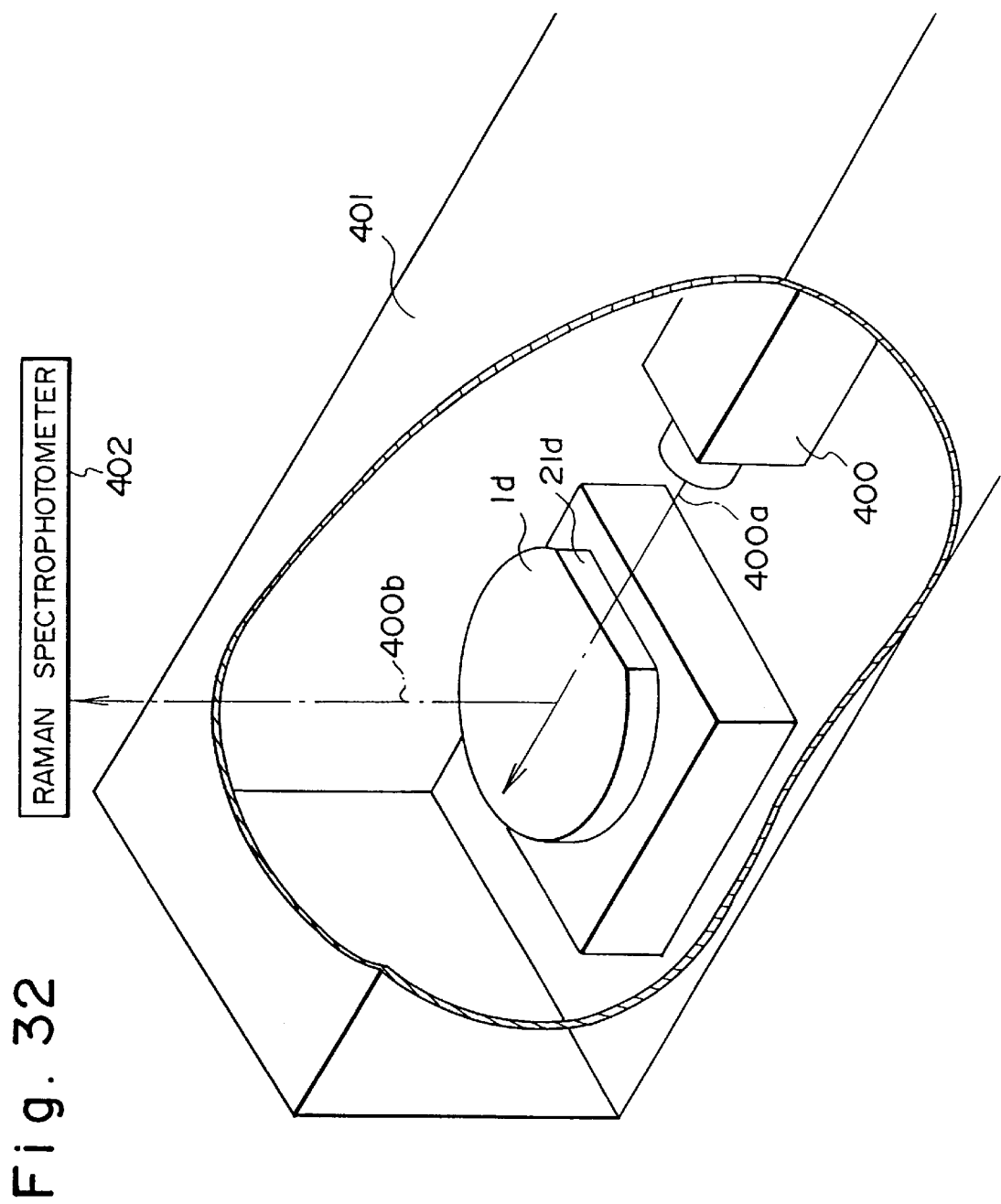
FIG. 32 shows a measuring system.

The piece 1d is also evaluated by the Raman spectroscopic analysis. A system for this evaluation is shown in FIG. 32. This system has a dark box 401, Ar laser light source 400 for emitting laser light 400a, being arranged in the dark box 401, and a Raman spectrophotometer 402 for detecting light 400b scattered in the piece 1d. The laser light beam 400a is introduced into the piece 1d through the side flat surface 21d, and the Raman scattering is occurred in the piece 1d and the scattered light 400b is emitted through the upper surface 21a. Consequently, since the piece 1d has the above-described shape, it can be evaluated by many system. The piece 1d may be applicable to measuring a transmittance of a glass as a standard sample.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 215096/1994 filed on Sep. 8, 1994 is hereby incorporated by reference.

What is claimed is:

1. A silica glass piece having two flat surfaces opposing each other, wherein,
    (a) each of said two flat surfaces has a surface roughness of 10 angstroms or less; and
    (b) the transmittance of said silica glass piece is not less than 0.910 cm$^{-1}$ and not more than 0.921 cm$^{-1}$ with respect to a light beam having a wavelength of 248 nm.

2. A silica glass piece according to claim 1, wherein an angle between said two flat surfaces is 30 second or less.

3. A silica glass piece according to claim 1 wherein an amount of undesired Ce is $4 \times 10^{12}$ atoms/cm$^2$ or less.

4. A silica glass piece having two flat surfaces opposing each other, wherein,
    (a) each of said two flat surfaces has a surface roughness of 10 angstroms or less; and
    (b) the transmittance of said silica glass piece is not less than 0.895 cm$^{-1}$ and not more than 0.908 cm$^{-1}$ with respect to a light beam having a wavelength of 193 nm.

5. A silica glass piece having two flat surfaces opposing each other, wherein,
    (a) each of said two flat surfaces has a surface roughness of 10 angstroms or less; and
    (b) the transmittance of said silica glass piece is not less than 0.9210 cm$^{-1}$ and not more than 0.9211 cm$^{-1}$ with respect to a light beam having a wavelength of 248 nm.

6. A silica glass piece according to claim 4, wherein the transmittance of said silica glass piece is not less than 0.905 cm$^{-1}$ and not more than 0.908 cm$^{-1}$ with respect to a light beam having a wavelength of 193 nm.

7. A silica glass piece according to claim 1, wherein said piece satisfies the following expression:

A+B<4368 nm where,

A is the distance between two maximally separated parallel virtual planes on one of said flat surfaces; and B is the distance between two maximally separated parallel virtual planes on the other of said flat surfaces is the distance between two maximally separated parallel virtual planes on one of said flat surfaces.

8. A silica glass piece according to claim 1, comprising:

two side surfaces continuous to each other, said two side surfaces connecting peripheries of said two flat surfaces, one of said side surfaces curving around the peripheries of said two flat surfaces, the other side surface being flat causing said silica glass piece to have the shape of flattened cylinder.

9. A silica glass piece according to claim 8, wherein the circumferential angle of said curving side surface is greater than 270°.

10. A piece having two flat surfaces opposing each other, wherein, (a) each of said two flat surfaces has a surface roughness of 10 angstroms or less; and (b) the transmittance of said piece is not less than 0.910 $cm^{-1}$ and not more than 0.921 $cm^{-1}$ with respect to a light beam having a wavelength of 248 nm.

11. A piece according to claim 10, wherein an angle between said two flat surfaces is 30 second or less.

12. A piece according to claim 10, wherein an amount of undesired Ce is $4 \times 10^{12}$ atoms/$cm^2$ or less.

13. A piece having two flat surfaces opposing each other, wherein, (a) each of said two flat surfaces has a surface roughness of 10 angstroms or less; and (b) the transmittance of said piece is not less than 0.895 $cm^{-1}$ and not more than 0.908 $cm^{-1}$ with respect to a light beam having a wavelength of 193 nm.

14. A piece having two flat surfaces opposing each other, wherein, (a) each of said two flat surfaces has a surface roughness of 10 angstroms or less; and (b) the transmittance of said piece is not less than 0.9210 $cm^{-1}$ and not more than 0.9211 $cm^{-1}$ with respect to a light beam having a wavelength of 248 nm.

15. A piece according to claim 10, wherein the transmittance of said piece is not less than 0.905 $cm^{-1}$ and not more than 0.908 $cm^{-1}$ with respect to a light beam having a wavelength of 193 nm.

16. A piece according to claim 10, wherein said piece satisfies the following expression:

A+B<4368 nm;

where;

A is the distance between two maximally separated parallel virtual planes on one of said flat surfaces; and B is the distance between two maximally separated parallel virtual planes on the other of said flat surfaces is the distance between two maximally separated parallel virtual planes on one of said flat surfaces.

17. A piece according to claim 10, comprising:

two side surfaces continuous to each other, said two side surfaces connecting peripheries of said two flat surfaces, one of said side surfaces curving around the peripheries of said two flat surfaces, the other side surface being flat causing said piece to have the shape of flattened cylinder.

18. A piece according to claim 17, wherein the circumferential angle of said curving side surface is greater than 270°.

* * * * *